US012690923B2

(12) United States Patent
Vaidya et al.

(10) Patent No.: US 12,690,923 B2
(45) Date of Patent: Jul. 28, 2026

(54) APPARATUS AND METHOD OF DETERMINING A CARDIAC IMPLANT SIZE

(71) Applicant: Anumana, Inc., Cambridge, MA (US)

(72) Inventors: Suthirth Vaidya, Bengaluru (IN);
Abhijith Chunduru, Bengaluru (IN);
Rakesh Barve, Bengaluru (IN)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 18/938,980

(22) Filed: Nov. 6, 2024

(65) Prior Publication Data

US 2026/0123992 A1 May 7, 2026

(51) Int. Cl.
*A61B 34/10* (2016.01)
*A61B 8/00* (2006.01)
*A61B 8/08* (2006.01)
*A61B 17/12* (2006.01)
*G06T 17/20* (2006.01)

(52) U.S. Cl.
CPC ............ *A61B 34/10* (2016.02); *A61B 8/0883* (2013.01); *A61B 8/466* (2013.01); *A61B 8/5223* (2013.01); *A61B 17/12122* (2013.01); *G06T 17/20* (2013.01); *A61B 2034/105* (2016.02); *A61B 2034/108* (2016.02); *G06T 2210/41* (2013.01)

(58) Field of Classification Search
None
See application file for complete search history.

(56) References Cited

U.S. PATENT DOCUMENTS

| | | | | |
|---|---|---|---|---|
| 9,406,129 B2 * | 8/2016 | Schilling | ................ | A61B 6/503 |
| 11,344,263 B2 * | 5/2022 | Villongco | .............. | A61B 34/10 |
| 2009/0281415 A1 * | 11/2009 | Cupps | .............. | G01R 33/56333 |
| | | | | 600/410 |
| 2012/0022843 A1 * | 1/2012 | Ionasec | ................... | G06T 13/20 |
| | | | | 703/11 |
| 2012/0232853 A1 * | 9/2012 | Voigt | ..................... | G16H 50/50 |
| | | | | 703/11 |
| 2015/0265162 A1 * | 9/2015 | Lavi | ...................... | G06T 7/0012 |
| | | | | 600/408 |

(Continued)

OTHER PUBLICATIONS

K Michiels et al; Automated MSCT Analysis for Planning Left Atrial Appendage Occlusion Using Artificial Intelligence Journal of interventional cardiology, vol. 2022, Apr. 27, 2022.

(Continued)

*Primary Examiner* — Patricia J Park
(74) *Attorney, Agent, or Firm* — CALDWELL LLC

(57) ABSTRACT

Described herein is an apparatus and method for determining a cardiac implant size. In some embodiments, an apparatus may include an ultrasonic imaging device, at least a processor, and a memory communicatively connected to the at least a processor, wherein the memory contains instructions configuring the at least a processor to, using the ultrasonic imaging device, collect a plurality of ultrasonic images, using a 3D cardiac model generation machine learning model trained on a training dataset comprising example ultrasonic images correlated with example 3D cardiac models, generate a 3D cardiac model based on the plurality of ultrasonic images, generate at least a cardiac measurement based on the 3D cardiac model, determine a cardiac implant size based on the at least a cardiac measurement, and display to a user the cardiac implant size.

20 Claims, 11 Drawing Sheets

(56) References Cited

U.S. PATENT DOCUMENTS

| | | | | |
|---|---|---|---|---|
| 2019/0090951 A1* | 3/2019 | Camus | | A61B 8/5261 |
| 2019/0130074 A1* | 5/2019 | Itu | | G06V 10/82 |
| 2020/0279643 A1 | 9/2020 | Srivastava et al. | | |
| 2021/0022806 A1 | 1/2021 | De Beule et al. | | |
| 2021/0350529 A1* | 11/2021 | Ayinde | | G06N 20/20 |
| 2023/0119535 A1 | 4/2023 | Michiels et al. | | |
| 2024/0013385 A1 | 1/2024 | Tominaga et al. | | |

OTHER PUBLICATIONS

Baravan Al-Kassou1 et al."A comparison of two-dimensional and real-time 3D transoesophageal echocardiography and angiography for assessing the left atrial appendage anatomy for sizing a left atrial appendage occlusion system: impact of volume loading"; DOI: 10.4244/EIJ-D-15-00543; Apr. 2017.

Michael Glikson et al.; "EHRA/EAPCI expert consensus statement on catheter-based left atrial appendage occlusion—an update"; DOI: 10.4244/EIJY19M08_01; Jan. 2020.

Nielsen-Kudsk, J, Berti, S, Caprioglio, F. et al. Intracardiac Echocardiography to Guide Watchman FLX Implantation: The ICE LAA Study. J Am Coll Cardiol Intv. Mar. 2023, 16 (6) 643-651. https://doi.org/10.1016/j.jcin.2022.10.024.

2024 Circle Cardiovascular Imaging Inc.; https://www.circlecvi.com/interventional-planning.

Watchman™ TruPlan™ software is developed and owned by Circle Cardiovascular Imaging Inc. (Calgary, AB, Canada), and Boston Scientific is the exclusive reseller of Watchman™ TruPlan™ software. SH-1414603-AA.

Eng MH, Wang DD, Greenbaum AB, Gheewala N, Kupsky D, Aka T, Song T, Kendall BJ, Wyman J, Myers E, Forbes M, O'Neill WW . . . Prospective, randomized comparison of 3-dimensional computed tomography guidance versus TEE data for left atrial appendage occlusion (PRO3DLAAO). Catheter Cardiovasc Interv. Aug. 1, 2018;92(2):401-407. doi: 10.1002/ccd.27514. Epub Feb. 1, 2018. PMID: 29388306.

Korsholm K, Berti S, Iriart X, Saw J, Wang DD, Cochet H, Chow D, Clemente A, De Backer O, Møller Jensen J, Nielsen-Kudsk JE. Expert Recommendations on Cardiac Computed Tomography for Planning Transcatheter Left Atrial Appendage Occlusion. JACC Cardiovasc Interv. Feb. 10, 2020;13(3):277-292. doi: 10.1016/j.jcin. 2019.08.054. Epub Oct. 30, 2019. PMID: 31678086.

Jessican Lamb, Ph.D; DHT8B: Division of Radiological Imaging Devices and Electronic Products; Trade/Device Name: TruPlan Computed Tomography (CT) Imaging Software; Jan. 18, 2023.

Watchman FLXTM Pro https://www.watchman.com/en-us-implanter/device/watchman-flx-pro.html.

Watchman FLXTM https://www.watchman.com/en-us-implanter/device/watchman-flx.html.

\* cited by examiner

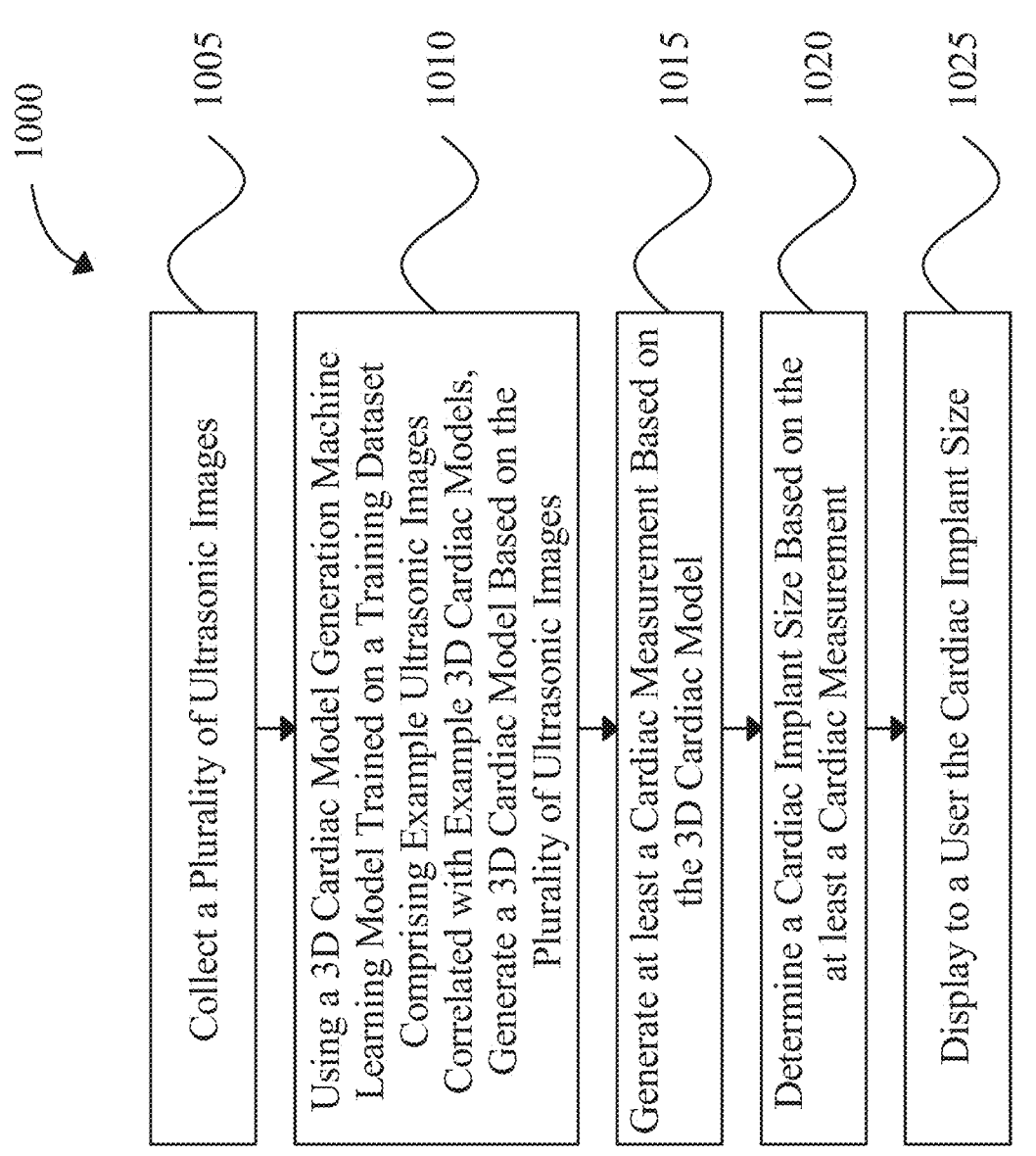

1000

1005 — Collect a Plurality of Ultrasonic Images

1010 — Using a 3D Cardiac Model Generation Machine Learning Model Trained on a Training Dataset Comprising Example Ultrasonic Images Correlated with Example 3D Cardiac Models, Generate a 3D Cardiac Model Based on the Plurality of Ultrasonic Images 1015 — Generate at least a Cardiac Measurement Based on the 3D Cardiac Model 1020 — Determine a Cardiac Implant Size Based on the at least a Cardiac Measurement 1025 — Display to a User the Cardiac Implant Size

FIG. 10

APPARATUS AND METHOD OF DETERMINING A CARDIAC IMPLANT SIZE

FIELD OF THE INVENTION

The present invention generally relates to the field of cardiac imaging. In particular, the present invention is directed to an apparatus and method of determining a cardiac implant size.

BACKGROUND

Computed tomography (CT) has been shown to be superior to 2D TEE in Watchman pre-procedural device sizing. As per the PRO3DLAAO clinical trial, the accuracy for 1st occluder device selection is 92% with CT vs. 27% with 2D-TEE, using the final implanted Watchman device size as the reference standard. The poor accuracy of the initial device selection results in longer procedures and usage of multiple devices until the implantation can be verified to be leakage-free. That is, an average of 2.5 devices is used with 2D TEE-based planning vs. 1.3 devices used with CT-based planning. However, computed tomography exposes subjects to radiation, and is often performed on a separate date, requiring multiple appointments and potentially reducing accuracy due to the time delay between when the data is captured and when it is used.

SUMMARY OF THE DISCLOSURE

In an aspect, described herein is an apparatus for determining a cardiac implant size. Such an apparatus may include an ultrasonic imaging device, at least a processor, and a memory communicatively connected to the at least a processor, wherein the memory contains instructions configuring the at least a processor to, using the ultrasonic imaging device, collect a plurality of ultrasonic images, using a 3D cardiac model generation machine learning model trained on a training dataset comprising example ultrasonic images correlated with example 3D cardiac models, generate a 3D cardiac model based on the plurality of ultrasonic images, generate at least a cardiac measurement based on the 3D cardiac model, determine a cardiac implant size based on the at least a cardiac measurement, and display to a user the cardiac implant size.

In another aspect, described herein is a method of determining a cardiac implant size, the method comprising, using at least a processor and an ultrasonic imaging device, collecting a plurality of ultrasonic images, using the at least a processor and a 3D cardiac model generation machine learning model trained on a training dataset comprising example ultrasonic images correlated with example 3D cardiac models, generating a 3D cardiac model based on the plurality of ultrasonic images, using the at least a processor, generating at least a cardiac measurement based on the 3D cardiac model, using the at least a processor, determining a cardiac implant size based on the at least a cardiac measurement, and using the at least a processor, displaying to a user the cardiac implant size.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention.

However, it should be understood that the present invention is not limited to the precise arrangements and instrumentalities shown in the drawings, wherein:

FIG. 10 is a flow diagram depicting an exemplary embodiment of a method of determining a cardiac implant size;

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, an apparatus and method for determining a cardiac implant size is disclosed. An apparatus may include an ultrasonic imaging device and a computing device. Such a computing device may receive ultrasonic images of a subject's heart, such as transesophageal echocardiograms (TEE) and/or intracardiac echo (ICE) images. A computing device may generate a 3D cardiac model by inputting ultrasonic images into a trained machine learning model. Such a machine learning model may be trained on a training dataset including ultrasonic images associated with 3D cardiac models generated based on historical computed tomography (CT) scan data. A 3D cardiac model generated by such a machine learning model may be used to determine a cardiac measurement, which may be used to determine, as examples, a cardiac implant size, a cardiac implant placement, and/or a degree to which a subject is a suitable candidate for receiving a cardiac implant. In some embodiments, such an apparatus or method may represent an improvement over existing techniques, at least because CT scans, which take time and involve exposing the subject to radiation, are not required, and TEE may obtain clear ultrasonic images due to the proximity of a probe to the heart.

Figure 1:
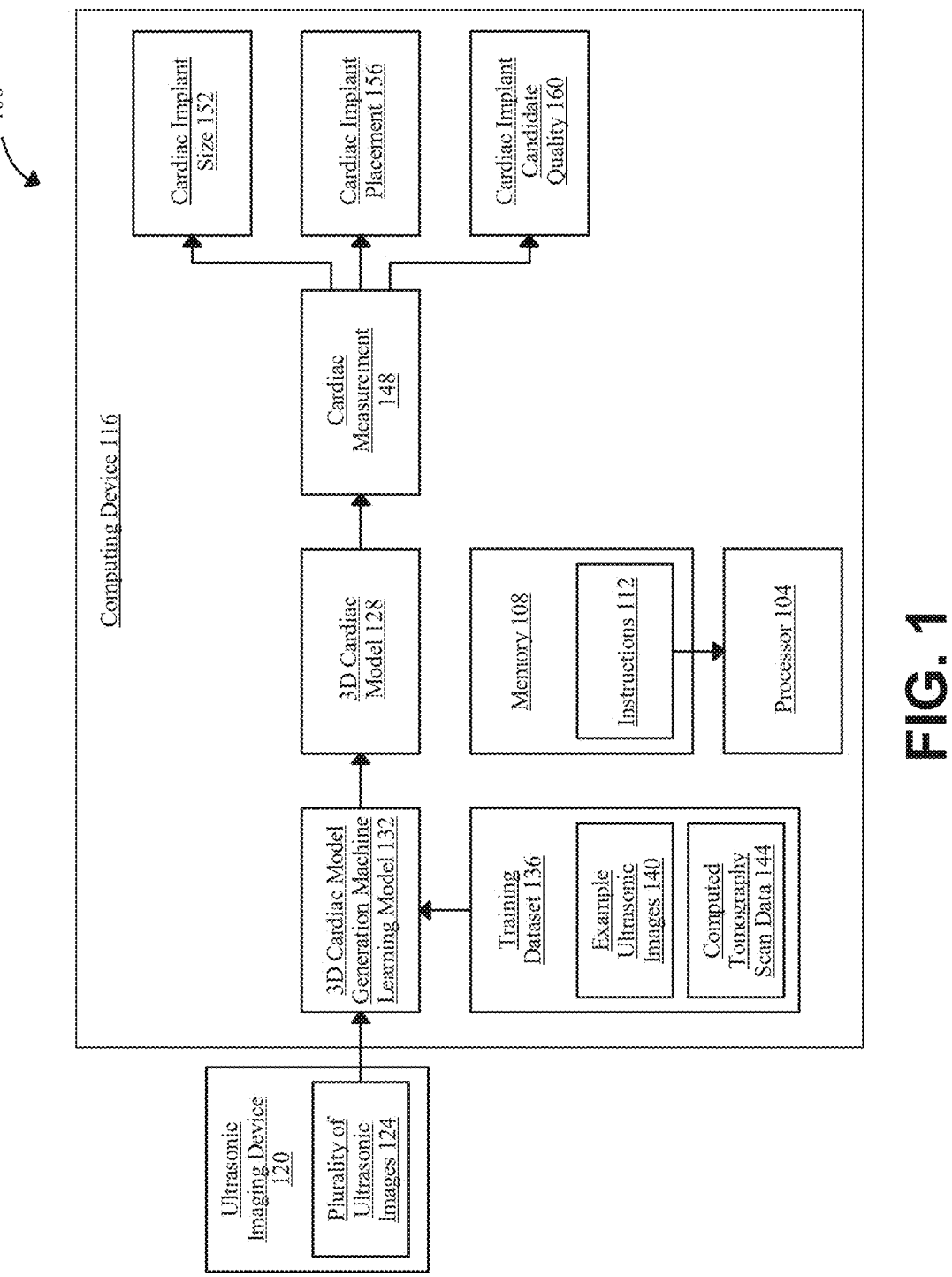
FIG. 1 is a diagram depicting an exemplary embodiment of an apparatus for determining a cardiac implant size.

Referring now to FIG. 1, an exemplary embodiment of an apparatus 100 for determining a cardiac implant size is illustrated. Apparatus 100 may include a computing device. Apparatus 100 may include a processor. Processor may include, without limitation, any processor described in this disclosure. Processor may be included in computing device. Computing device may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device may include a single computing device operating independently, or may include two or more computing device operating in concert, in parallel, sequentially or the like; two or more computing devices may be included together in a single computing device or in two or more computing devices. Computing device may interface or communicate with one or more additional devices as described below in further detail via a network interface device. Network interface device may be utilized for connecting computing device to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device.

Still referring to FIG. 1, in some embodiments, apparatus 100 may include at least a processor 104 and a memory 108 communicatively connected to the at least a processor 104, the memory 108 containing instructions 112 configuring the at least a processor 104 to perform one or more processes described herein. Computing device 116 may include processor 104 and/or memory 108. Computing device 116 may be configured to perform one or more processes described herein.

Still referring to FIG. 1, computing device 116 may include but is not limited to, for example, a computing device or cluster of computing devices in a first location and a second computing device or cluster of computing devices in a second location. Computing device 116 may include one or more computing devices dedicated to data storage, security, distribution of traffic for load balancing, and the like. Computing device 116 may distribute one or more computing tasks as described below across a plurality of computing devices of computing device, which may operate in parallel, in series, redundantly, or in any other manner used for distribution of tasks or memory between computing devices. Computing device 116 may be implemented, as a non-limiting example, using a "shared nothing" architecture.

Still referring to FIG. 1, computing device 116 may be designed and/or configured to perform any method, method step, or sequence of method steps in any embodiment described in this disclosure, in any order and with any degree of repetition. For instance, computing device 116 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 116 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, as used in this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Still referring to FIG. 1, processor may include ultrasonic imaging device 120, and/or may be configured to collect plurality of ultrasonic images 124. Plurality of ultrasonic images 124 may include, without limitation, a two-dimensional image. As used herein, an "ultrasonic image" is an image generated as a function of a reflection of a sound wave off of a structure. As used herein, an "ultrasonic imaging device" is a device configured to collect ultrasonic images. Non-limiting examples of ultrasonic images and/or imaging techniques include intracardiac echo (ICE) images, transthoracic echocardiograms (TTE), transesophageal echocardiograms (TEE), and point of care ultrasound (POCUS). In some embodiments, plurality of ultrasonic images 124 may include a TEE image. In some embodiments, a TEE image may include a 2D TEE. In some embodiments, a TEE image may include a 3D TEE. In some embodiments, plurality of ultrasonic images 124 may include an ICE image. In some embodiments, a set of ultrasonic images of the patient's organ may include an image selected from the list consisting of a transesophageal echocardiogram image, a transthoracic echocardiogram image, and a point-of-care ultrasound image. An ultrasonic image of plurality of ultrasonic images 124 may depict an organ and/or tissue of a subject. An ultrasonic image of plurality of ultrasonic images 124 may depict a heart, lung, spleen, liver, kidney, muscle, skeleton, intestine, stomach, vein, and/or artery. In some embodiments, an ultrasonic image may depict a heart, and/or a left atrium, left atrial appendage, left ventricle, right ventricle, and/or a right atrium of a heart.

Still referring to FIG. 1, in some embodiments, an ultrasonic image may include transesophageal echocardiogram (TEE) image. In some embodiments, a TEE image may include a view of an ostial diameter and/or length. In some embodiments, plurality of ultrasonic images 124 may include ultrasonic images captured at the same position, and different orientations with respect to a subject's heart. In some embodiments, a TEE image may include a view of an ostial diameter and/or length from one or more angles on a mid-esophageal view. As examples, a TEE image may include a view of a subject's heart and/or an ostial diameter and/or length from 1, 2, 3, 4, 5, 6, 7, 8, 9, or 10 different angles on a mid-esophageal view. In a non-limiting example, a TEE image may include a view of a subject's heart and/or an ostial diameter and/or length from 4 different angles (0°, 45°, 90°, 135°) on a mid-esophageal view. In some embodiments, angles of images may describe a rotational position of an ultrasound transducer relative to a subject's heart. In additional non-limiting examples, a TEE image may include a view of a subject's heart and/or an ostial diameter and/or length from 0° (which may provide a four chamber view), 45- 60° (which may provide a two chamber view and in some embodiments may be used to identify a thrombus), 90° (which may provide a long-axis view), 120-135° (which may provide a long-axis view of a left atrial appendage) and/or 135-160° (which may provide an aortic valve long axis view) on a mid-esophageal view. In some embodiments, an ostial diameter and/or length includes an ostial diameter and/or length of a left atrial appendage (LAA) of a heart and/or another location at which a cardiac implant may be placed. In some embodiments, TEE image may include a view of an ostial diameter and/or length from 4 different angles, such as, as a non-limiting example, 0°, 45°, 90°, and 135°. TEE imaging is discussed further with respect to FIG. 5.

Still referring to FIG. 1, in some embodiments, an ultrasonic image may include an intracardiac echocardiography (ICE) image. As used herein, an "ICE image" is an ultrasound image obtained from within the heart's chambers or blood vessels. In some cases, ICE images may be captured using a specialized catheter equipped with an ultrasound transducer that is inserted into the body and guided to the heart of subject. In an embodiment, an ultrasound image may provide a detailed and real-time visualization of cardiac anatomy. ICE images may also include internal structures, functions, and blood flow patterns of the heart of a subject. Plurality of ultrasonic images 124 may be related in terms of content, time of capture, sequence, or any other relevant parameters described herein. In a non-limiting example, each image of plurality of ultrasonic images 124 may represent a particular view, angle, or perspective of an object, subject, or scene, and may be in two-dimensional (2D) or 3D format. Images of plurality of ultrasonic images 124 may include, without limitation, any two-dimensional or three-dimensional images of any anatomy or anatomical structure, including without limitation images of any internal organ, tissue including without limitation muscular, connective tissue, epithelial tissue, and/or nervous tissue, bone, and/or any other element that may be imaged within a human and/or animal body.

Still referring to FIG. 1, in a non-limiting example, structures of a heart of a subject which may be imaged may include chambers (e.g., four chambers including left and right atria and left and right ventricles), valves (i.e., the structures that regulate blood flow between chambers and vessels, including mitral, tricuspid, aortic, and pulmonary valves), vessels (e.g., aorta, pulmonary arteries and veins, and coronary arteries), conduction system (i.e., a network of specialized cells that control the heart's electrical activity and rhythm), muscular and connective tissues (e.g., heart's muscular walls, septa, any other connective tissues that provide structural integrity and enable contraction), LAA and other appendages, pathological features (e.g., any abnormalities, defects, and/or the like), and/or other components of a heart.

Still referring to FIG. 1, as used in this disclosure, a "subject" refers to an individual organism. In an embodiment, subject may include a human, such as a human in need of a cardiac implant. A cardiac implant may include a left atrial appendage occlusion (LAAO) device. A cardiac implant may include a watchman device. A watchman device may fit in the left atrium of a subject and form a barrier against blood clots in order to reduce the risk of stroke. Different patients may receive different size devices, and cardiac measurements made as described herein may be used to determine which size device to give to a particular subject.

Still referring to FIG. 1, in an embodiment, each ultrasonic image of plurality of ultrasonic images 124 may include a particular view of subject's heart's chambers, valves, vessels, and/or the like. In a non-limiting example, plurality of ultrasonic images 124 may include multiple views e.g., different angles and perspectives of a subject's heart. In another embodiment, plurality of ultrasonic images 124 may be arranged in a temporal sequence. In a non-limiting example, plurality of ultrasonic images 124 may include a series of images captured over time, allowing for an observation of dynamic cardiac functions such as beating, blood flow, and/or the like. In some cases, each ultrasonic image of plurality of ultrasonic images 124 may include a corresponding timestamp, wherein the timestamp may include an indicator showing a date and time of when the corresponding ultrasonic image was taken.

Still referring to FIG. 1, in some embodiments, plurality of ultrasonic images 124 may be received from an electronic health record database. For example, plurality of ultrasonic images 124 may be collected at a first point in time, stored in an electronic health record database, and later used in further steps of a process described herein. In some embodiments, plurality of ultrasonic images 124 may be collected using an ultrasonic imaging device as part of a procedure for administering a cardiac implant to a subject.

Still referring to FIG. 1, in some embodiments, receiving plurality of ultrasonic images 124 may involve one or more image preprocessing steps. In some cases, processor 104 may be configured to calibrate one or more ultrasonic images of plurality of ultrasonic images 124 by correcting for distortions and/or ensuring accurate spatial representation of a heart of a subject. In a non-limiting example, processor 104 may select one or more reference objects within ultrasonic image which need calibration to correct spatial distortions. In some cases, processor 104 may be configured to place a phantom with pre-determined dimensions in an ultrasonic image and adjust ultrasonic image until the phantom's dimensions are accurately represented. In another non-limiting example, an ultrasonic images' brightness and/or contrast may be adjusted by processor 104 to ensure that echogenicity (reflectivity) of the tissues is accurately represented. One or more tissues with known echogenicity may be selected by processor 104 as reference tissues to adjust corresponding portions of the one or more ultrasonic images. In other cases, standardized correction curves may be applied in order to correct the echogenicity of ultrasonic images. As an ordinary person skilled in the art, upon reviewing the entirety of this disclosure, may be aware of various calibration techniques, such as, without limitation, temporal calibration, geometric calibration, among others that can be used by processor 104 to preprocess plurality of ultrasonic images 124.

Still referring to FIG. 1, receiving plurality of ultrasonic images 124 may include perform image segmentation on or more ultrasonic images of plurality of ultrasonic images 124. In some cases, image segmentation may include separating specific structures or regions of interest (ROI) from the background or other structures in a given ultrasonic image. In a non-limiting example, processor 104 may be configured to use edge detection algorithms to outline the heart chambers, separating them from surrounding tissues. One or more filters may be applied to highlight the boundaries between different types of tissues during the segmentation. In another non-limiting examples, valves and vessels may also be segmented by applying thresholding techniques. Processor 104 may be configured to set an intensity threshold based on the known echogenicity of blood and vessel walls and select pixels or regions having intensity below or above the intensity threshold from the given ultrasonic image. In some cases, one or more machine learning models may be used to perform image segmentations, for example, and without limitation, a U-net (i.e., a convolution neural network containing a contracting path as an encoder and an expansive path as a decoder, wherein the encoder and the decoder forms a U-shaped structure).

Still referring to FIG. 1, processor may be configured to generate a 3D data structure representing a heart of a subject as a function of plurality of ultrasonic images 124. In a non-limiting example, 3D data structure may include a 3D voxel occupancy representation (VOR). As used in this disclosure, a "3D voxel occupancy representation (VOR)" of anatomy is a 3D digital representation of a spatial structure of the anatomy, wherein the representation is composed of a plurality of discrete volumetric elements known as voxels. A "voxel," for the purpose of this disclosure, is a 3D equivalent of a pixel in 2D imaging. While a pixel represents a point in a 2D image and may include properties such as color and/or brightness, a voxel may represent a volume in a 3D space and may include additional properties such density/occupancy as described below. In an embodiment, each voxel of plurality of voxels within 3D VOR may represent a specific portion of a heart. In some cases, voxel may be a smallest distinguishable box-shaped part (i.e., 1px·1px·1px) of a three-dimensional image. In some cases, each voxel of plurality of voxels within VOR may be represented as a cube or rectangular prism (although other shapes may be used in specialized applications). Each voxel may include a size that determines a resolution of the 3D image or model. In an embodiment, smaller voxels may provide higher resolution; however, it may require more computational resources (e.g., RAM) for processor 104 to process.

Still referring to FIG. 1, each voxel of plurality of voxels within VOR may include one or more embedded values. As used herein, "embedded values" refers to specific numerical or categorical data associated with each voxel. In some cases, embedded values may represent various attributes or characteristics of the corresponding portion of structure that voxel represents. In a non-limiting example, embedded values may include density values, intensity values, texture information, or any other quantitative measures that provide insights into the underlying tissue. Such embedded values may be derived from set of ultrasonic images or other imaging modalities used to generate data structure. In some cases, embedded values may be utilized, by processor 104, to differentiate between different types of tissues, such as myocardial tissue, blood vessels, or chambers. Embedded values may also facilitate the visualization of dynamic cardiac functions, for example, and without limitation, blood flow or heart beating by encoding temporal information such as timestamps within plurality of voxels.

Still referring to FIG. 1, in an embodiment, each voxel of plurality of voxels may include a presence indicator. As used in this disclosure, a "presence indicator" refers to a data element that indicates a presence or absence (i.e., occupancy) of tissue within that portion. In some cases, and without limitation, presence indicator may include an occupancy status as one of the embedded values described herein. Portion may include a specific location within 3D space where data structure is generated; for instance, and without limitation, a coordinate in 3D space represented in a tuple such as (x, y, z). In an embodiment, 3D VOR may provide a spatial framework that allows for the modeling and visualization of structure in 3D space. In some cases, 3D data structure may include a plurality of layers or slices (either horizontal [e.g., xy plane] or vertical [e.g., xz or yz plane depends on the view direction]), wherein each layer or slices of the plurality of layers or slices is corresponding to a different cross-sectional view of a structure of subject, and collectively forming a comprehensive 3D depiction of the structure. In a non-limiting example, 3D VOR having plurality of voxels with presence indicators may indicate whether each voxel in 3D space may be occupied by a part of a structure of subject. A binary value such as 0 or 1 may be configured as presence indicator to show either a pixel of 3D space is occupied (e.g., 1) or empty (e.g., 0). In should be noted that other values may be used as presence indicator such as a Boolean value e.g., TRUE or FALSE.

Still referring to FIG. 1, one or more embedded values, such as, without limitations, occupancy, or density, may be derived from plurality of ultrasonic images 124 described herein by processor 104. In a non-limiting example, determining occupancy status of each voxel of plurality of voxels may include converting set of ultrasonic images to a set of binary images and determining occupancy status of each voxel as a function of the structure of interest's binary value. In some cases, occupancy status may include a value representing the likelihood of occupancy of the corresponding tissue. In another non-limiting example, density may be calculated, by processor 104, for each voxel as a function of the echogenicity of one or more pixels on a given ultrasonic image, wherein, the brightness of the given ultrasonic image may be analyzed since different tissues reflect ultrasound waves differently.

Still referring to FIG. 1, generating 3D data structure of a subject's heart may include generating a 3D array. In some cases, processor 104 may divide 3D space into a grid of plurality of voxels, each with specific x, y, and z coordinates as embedded values. Each element of 3D array may correspond to a voxel. In some cases, 3D array may allow for easy access and manipulation of plurality of voxels, enabling various analyses, visualizations, and transformations either described or not described herein. In a non-limiting example, embedded values may include a density of the tissue at a specific location of a patient's body derived from one or more ultrasonic images of plurality of ultrasonic images 124.

Still referring to FIG. 1, 3D data structure of structure may include a 3D grid configured to map presence indicators and/or other embedded values described herein of plurality of voxels (e.g., tissue density, blood flow velocity, echogenicity or acoustic properties, and any other biophysical properties). As used in this disclosure, a "3D grid" refers to a 3D data structure that divides a given volume (e.g., volume of a structure) into a plurality of discrete units called cells (i.e., volume elements). In an embodiment, each cell within 3D grid may be associated with a distinct voxel. Mapping presence indicators or other embedded values may include assigning each presence indicator or embedded value to each point within 3D grid such as corners of each corresponding cell. Such values may be derived from plurality of ultrasonic images 124 as described above.

Still referring to FIG. 1, cells may be continuous, meaning that one or more cells may represent one or more continuous regions of space rather than discreate, separate units. In a non-limiting example, instead of being uniform, mapped presence indicator and/or other embedded values may vary continuously across different cells or cell's volume. In such embodiment, processor 104 may use interpolation to estimate other (unknown) embedded values within a range based on existing values such as known embedded values at specific points, thereby allowing for smooth transitions between cells. Exemplary interpolation methods may include, without limitation, linear interpolation, cubic interpolation, and/or the like. For example, and without limitation, if the corners of a cell have known values interpolation can be used to estimate the values at any point within the cell based on those corner values.

Still referring to FIG. 1, 3D data structure of a heart may include a 3D grid having a plurality of cells e.g., voxels, wherein each cell may contain a continuous range of values representing tissue density, blood flow velocity, or other properties (i.e., embedded values). Processor 104 may be configured to apply trilinear or tricubic interpolation to estimate tissue density within each cell based on presence indicator or other known values at the cell's boundaries, since tissue densities change gradually; Such 3D grid may provide a smooth, continuous representation of heat's internal structures, allowing for more nuanced analysis and visualization as described below. In a further embodiment, 3D grid with continuous cells may be additionally used in fluid dynamics simulations.

Still referring to FIG. 1, presence indicators and/or other embedded values may be mapped to a 3D grid as a function of array masking. In a non-limiting example, processor 104 may generate a mask e.g., a binary array that defines which voxels or cells are affected. Mask may be used to select or modify specific voxels or cells based on certain attributes; for instance, and without limitation, processor 104 may use a mask to isolate the LA within the heart focusing the analysis on that specific region. Such mask may include criteria defined by specific density thresholds that distinguish the LA's tissue (i.e., voxels representing LA in 3D grid) from surrounding structures (i.e., neighboring voxels). In some cases, such mask may further include a binary mask, wherein each voxel in the 3D grid may be assigned a first presence indicator such as 1 if the voxel meets the criteria for the LA and a second presence indicator such as 0 if it does not. In some embodiments, mask may be directly applied to 3D grid, selecting, or modifying voxels or cells, thereby enabling processor 104 to highlight, exclude, or otherwise manipulate specific parts of a heart within 3D grid. Processor 104 may then perform an element-wise multiplication between 3D grid and the mask. Continuing from the previous non-limiting example, voxels corresponding to the LA (wherein the mask value is 1) may retain their original values, while other voxels (where the mask value is 0) may be set to 0 or other specific value (i.e., excluded or masked out).

Still referring to FIG. 1, in some embodiments, 3D grid may include one or more spatial features extracted from plurality of ultrasonic images 124. As used in this disclosure, "spatial features" are specific characteristics or attributes related to the spatial arrangement, shape, size, texture, or orientation of structures within a 3D space. In some cases, spatial features may include one or more embedded values described herein and their combinations thereof. In a non-limiting example, spatial feature may be represented numerically as a vector, a metric or other mathematical constructs that capture specific spatial characteristics. In some cases, spatial features may also be visualized as contours, surfaces, or other geometric representations. In an embodiment, spatial features may be extracted using edge detection, texture analysis, or other image processing techniques (e.g., cleaning and enhancing images, image segmentation, and/or the like). In another embodiment, one or more machine learning models, such as convolutional neural networks (CNNs) as described in further detail below, may be used to extract complex spatial features.

Still referring to FIG. 1, in a non-limiting example, one or more spatial features may include one or more shape features (i.e., characteristics related to the shape of specific structures), such as curvature, surface area, volume, and/or the like. In another non-limiting example, one or more spatial features may include one or more texture features (i.e., characteristics related to the texture or pattern within tissues, as seen in plurality of ultrasonic images 124), such as gray-level co-occurrence matrix (GLCM) features representing the texture of heart muscle tissue. In another non-limiting example, one or more spatial features may include one or more orientation features (i.e., characteristics related to the orientation or alignment of structures), such as the angle or alignment of the septum within the heart. In a further non-limiting example, one or more spatial features may include one or more edge and boundary features (i.e., Characteristics related to the edges or boundaries between different structures), such as edge detection features highlighting the boundary between the myocardium and the cardiac chambers. As an ordinary person skilled in the art, upon reviewing the entirety of this disclosure, will be aware of various spatial features extracted from plurality of ultrasonic images 124 consistent with this disclosure.

Still referring to FIG. 1, apparatus 100 may determine 3D cardiac model 128 as a function of plurality of ultrasonic images 124. As used herein, a "3D cardiac model" is a 3D representation of a subject's heart. In some embodiments, apparatus 100 may determine 3D cardiac model 128 using 3D cardiac model generation machine learning model 132. 3D cardiac model generation machine learning model 132 may be trained to interpret ultrasonic images and/or generate 3D cardiac models 128 by learning relationships between ultrasonic images and corresponding computed tomography (CT) scan data. 3D cardiac model generation machine learning model 132 may be trained using a supervised learning algorithm. 3D cardiac model generation machine learning model 132 may include a neural network. 3D cardiac model generation machine learning model 132 may be trained on a training dataset 136 including example ultrasonic images 140, associated with example 3D cardiac models. Example ultrasonic images 140 may be generated based on historical CT scan data 144. For example, a 3D model generated based on CT scan data may be used to determine what ultrasonic images would contain when taken from varying perspectives. Training dataset 136 may be obtained by, for example, associating historical ultrasonic images with historical CT scan based 3D cardiac models. Once 3D cardiac model generation machine learning model 132 is trained, it may be used to determine 3D cardiac model 128. Apparatus 100 may input plurality of ultrasonic images 124 into 3D cardiac model generation machine learning model 132, and apparatus 100 may receive 3D cardiac model from 3D cardiac model generation machine learning model 132.

Still referring to FIG. 1, in some embodiments, a training dataset may be generated by correlating an instance of computed tomography scan data with one or more historical ultrasonic images as a function of a medical record and a language model. For example, a language model may be used to interpret a medical record and/or determine whether an instance of computed tomography scan data should be associated with a historical ultrasonic image in a training dataset. For example, a language model may be used to interpret language of a medical record, and the output of the language model may be used to identify whether a medical event has taken place between when the historical ultrasonic image was taken and when the historical computed tomography scan data was recorded, such that they are not to be associated in a training dataset. In another example, a language model may be used to interpret language of a medical record, and the output of the language model may be used to identify whether historical ultrasonic image and historical computed tomography scan data were recorded in a sufficiently short time, such that they are associated in a training dataset. In some embodiments, a training dataset may be identified by generating a synthetic ultrasonic image as a function of an instance of computed tomography scan data.

Still referring to FIG. 1, in some embodiments, training dataset 136 may include 3D cardiac models including computed tomography (CT) based 3D model. As used in this disclosure, a "computed tomography (CT) based 3D model" is a 3D representation of a structure that is created using data from CT scans. In some embodiments, a computed tomography (CT) based 3D model may include a 3D representation of a structure and surrounding structures that is created using data from CT scans. Computed Tomography is a medical imaging technique that uses X-rays to capture cross-sectional images (slices) of the body. By taking a plurality of slices, a CT scan creates a detailed 3D representation of the internal structure. In an embodiment, CT-based 3D model may include 3D representations of the heart including chambers, valves, blood vessels, and surrounding tissues. CT-based 3D models may be generated using existing techniques in the field as described above such as, without limitation, FAM, cardiac CT merging, among others.

Still referring to FIG. 1, processor 104 may be configured to receive at least an ultrasound localization datum. As used in this disclosure, an "ultrasound localization datum" is a unit of information that represents a position and/or angle of an ultrasound device. In some cases, ultrasound device may have incorporated one or more position sensors (e.g., accelerometers, gyroscope, inertial measurement units, magnetics location sensors, and the like) and/or be incorporated with an localization system. In some cases, one or more of ultrasound device and localization system communicates at least an ultrasound localization datum to processor 104. Processor may be configured to generate, using 3D cardiac model generation machine learning model, the 3D cardiac model as a function of at least an ultrasound localization datum Still referring to FIG. 1, processor 104 may be configured to generate a 3D voxel occupancy representation (VOR) representing a cardiac shape as a function of plurality of ultrasonic images and 3D cardiac model generation machine learning model trained. In some versions, processor 104 may generate a mesh representing cardiac shape as a function of 3D voxel occupancy representation. Processor 104 may be configured to display, using display, a mesh to a user.

Still referring to FIG. 1, processor 104 may be configured to calculate a level of uncertainty at a plurality of locations on 3D cardiac model. In some cases, plurality of locations may include a high uncertainty region. Processor 104 may be configured to receive a subsequent plurality of ultrasonic images of cardiac anatomy corresponding to a high uncertainty region of 3D cardiac model. In some cases, subsequent plurality of ultrasonic images may be captured using ultrasonic imaging device (e.g., ICE, TEE, TTE, and/or POCUS), as a function of high uncertainty region. Processor 104 may be configured to generate a subsequent 3D cardiac model as a function of subsequent plurality of ultrasonic images. Additionally disclosure related to calculating a level of uncertainty may be found in U.S. patent application Ser. No. 18/426,604, filed on Jan. 30, 2024, and entitled "APPARATUS AND METHOD FOR GENERATING A THREE-DIMENSIONAL (3D) MODEL OF CARDIAC ANATOMY BASED ON MODEL UNCERTAINTY," U.S. patent application Ser. No. 18/818,152 filed on Aug. 28, 2024, and entitled "APPARATUS AND METHOD FOR GENERATING A THREE-DIMENSIONAL (3D) MODEL OF PATIENTS ORGAN," U.S. patent application Ser. No. 18/395,087, filed on Dec. 22, 2023, and entitled "APPARATUS AND METHOD FOR GENERATING A THREE-DIMENSIONAL (3D) MODEL OF CARDIAC ANATOMY WITH AN OVERLAY," U.S. patent application Ser. No. 18/818,311, filed on Aug. 28, 2024, and entitled "APPARATUS AND METHOD FOR GENERATING A THREE-DIMENSIONAL (3D) MODEL WITH AN OVERLAY," each of which are incorporated in this disclosure by reference in their entirety.

Still referring to FIG. 1, a location on 3D cardiac model may refer to each voxel of plurality of voxels, cells, geometric marker, and all other identifying markers/data points of a model as described throughout this disclosure. A plurality of locations may refer to the surface of heart model, such as a set of pixels or a region on a model. "Uncertainty," as used herein, refers to the lack of confidence or precision in a model's predictions. In some cases, the level of uncertainty may be derived from variability within the distribution of shape parameters, image quality assessment, measurement errors and/or the like. In a non-limiting example, greater changes in heart geometry (indicated by the plurality of shape parameters) may correspond to a greater level of uncertainty at that location. This may be used to inform clinical decisions, for example, areas of high uncertainty may be avoided when planning a pathway for surgical intervention or additional imaging may be requested to reduce uncertainty in critical areas.

Still referring to FIG. 1, levels of uncertainty may refer to categories of uncertainty such as epistemic uncertainty, aleatoric uncertainty, model parameter uncertainty, pixel-wise uncertainty, boundary uncertainty, uncertainty in time series data, predictive uncertainty, systematic uncertainty, model output uncertainty, and the like. Epistemic uncertainty arises from a lack of knowledge or information. For example, limited training data for certain cardiac pathologies may contribute to higher epistemic uncertainty. Aleatoric uncertainty, also known as data uncertainty, results from inherent randomness or variability in the data. For example, variability in patient's organ among different patients or imaging modalities introduces aleatoric uncertainty. Model Parameter Uncertainty is uncertainty associated with the model parameters, indicating how well the model has learned the underlying patterns in the training data. For example, variations in model parameters due to the stochastic nature of the optimization process contribute to parameter uncertainty. Pixel-wise Uncertainty is associated with individual pixels in the image. It provides a confidence measure for each pixel in the segmentation mask. For example, certain regions of the heart may be more challenging to segment accurately, leading to higher pixel-wise uncertainty. Boundary Uncertainty is related to the boundaries between different structures or regions in the image. For example, the precise delineation of the endocardium or epicardium may be uncertain in regions where the boundaries are not well-defined. Regarding uncertainty in Time Series Data, in tasks involving sequential data, such as cardiac imaging over time, uncertainty can be related to variations in the temporal dimension. For example, segmentation of dynamic structures like the beating heart involves handling uncertainty associated with different phases of the cardiac cycle. Predictive Uncertainty is uncertainty in the model's predictions for unseen data points. For example, when the model encounters a novel pathology or an atypical cardiac structure, predictive uncertainty measures its confidence in providing accurate segmentation. Systematic Uncertainty is uncertainty stemming from systematic errors or biases in the data collection process or the model architecture. For example, if the training data is biased towards a specific demographic, the model may exhibit uncertainty when applied to a more diverse patient population. Model Output Uncertainty is uncertainty associated with the actual output of the model, indicating how confident the model is in its segmentation predictions. For example, the model may output a segmentation mask with a probability or confidence score for each pixel, reflecting the uncertainty associated with that pixel's classification.

Still referring to FIG. 1, a level of uncertainty may include a degree, statistical measure, percentage, or variable whether linguistic or numerical, and the like identifying a range of uncertainty. For example, Processor 104 may generate probability scores/confidence scores for locations of a model, indicating the model's confidence in its predictions. Calibration plots can be used to assess how well these confidence scores align with the true accuracy. Processor 104 may perform a threshold analysis to investigate how varying decision thresholds for classification or segmentation affects the trade-off between sensitivity and specificity in uncertain regions. Threshold analysis may include task-specific metrics for clinical relevance. For example, in cardiac image segmentation, critical regions like the myocardium may have stricter uncertainty thresholds compared to less critical regions. Processor 104 may implement Bayesian Neural Networks (BNNs) to perform posterior predictive checks to evaluate the agreement between the model's predictions and the observed data, such as data store, considering the uncertainty represented by the posterior distribution in Bayesian frameworks. In various embodiments, a level of uncertainty 160 may be metrics determined by processor 104, such as Pixel-wise Uncertainty Metrics, Boundary Displacement Error (BDE), Uncertainty-Aware Loss Functions, Calibration Metrics, and the like.

Still referring to FIG. 1, in some embodiments, a level of uncertainty may be determined using Monte Carlo dropout. Monte Carlo dropout may include running a neural network multiple times using different dropout configurations. Each dropout configuration may include turning off turning off one or more nodes of a neural network. Monte Carlo dropout may be used to, for example, determine mean and variance parameters. In some embodiments, such a variance parameter may be used as a level of uncertainty.

Still referring to FIG. 1, in some embodiments, a level of uncertainty may be determined using deep ensembles. A deep ensemble may include a plurality of machine learning models. An input may be applied to a plurality of machine learning model, and their outputs may be combined. For example, an average and/or variance of outputs of a plurality of models may be found. A level of uncertainty may be determined based on such variance.

Still referring to FIG. 1, processor 104 may be configured receive a 3D cardiac implant model representing a cardiac implant. As used in this disclosure, a "3D cardiac implant model" is a three-dimensional representation (i.e., image) of a cardiac implant. In some cases, 3D cardiac implant model may be represented as a statistical shape model, a mesh model, a point cloud, a VOR, or the like. In some cases, a 3D cardiac model may be generated according to any machine learning process described in this disclosure. In some cases, 3D cardiac implant model may be downloaded from a repository. Processor 104 may be configured to display, using display, 3D cardiac implant model with 3d cardiac model. In some cases, processor 104 may be configured to position 3D cardiac implant model relative 3D cardiac model. Receiving, position, and displaying a 3D cardiac implant model may be performed using systems and methods described in detail in U.S. patent application Ser. No. 18/648,176, filed on Apr. 26, 2024, and entitled "APPARATUS AND METHODS FOR VISUALIZATION WITHIN A THREE-DIMENSIONAL MODEL USING NEURAL NETWORKS" which is incorporated in this disclosure in its entirety by reference.

Still referring to FIG. 1, processor 104 may be configured to generate a set of shape parameters based on plurality of ultrasonic images 124. As used in this disclosure, a "set of shape parameters" refers to a collection of numerical values or descriptors that quantitatively represent the geometric or morphological characteristics of a heart. In some embodiments, a set of shape parameters may represent a shape of a heart. In a non-limiting example, set of shape parameters may include information and/or metadata calculated, determined, and/or extracted from set of ultrasonic images, such as, dimensions, angles, curvatures, surface areas, texture, symmetry, and/or the like. In other embodiments, processor 104 may be configured to parameterize features (e.g., edges, textures, contours, and any other characteristics that describe a subject's heart) extracted from plurality of ultrasonic images 124 using a convolutional neural network as described herein. Such parameterization may involve processor 104 to derive one or more shape parameters including one or more morphological descriptors that quantitatively describe a heart based on extracted features. In some cases, processor 104 may be configured to use principal component analysis (PCA) to reduce the dimensionality of set of shape parameters, allowing processor 104 to focusing on the most informative shape parameters of a set of shape parameters in further processing steps as described below.

Still referring to FIG. 1, in a non-limiting example, set of shape parameters may be generated based on plurality of ultrasonic images 124 using a shape identification model. Generating a set of shape parameters may include receiving structure training data, wherein the structure training data may include a plurality of image sets as inputs correlated to a plurality of shape parameter sets as outputs. In some cases, structure training data may be received from a Data store. For example, and without limitation, structure training data may be used to show each ultrasonic image may indicate a particular set of shape parameters. In some embodiments, structure training data may include historical ultrasonic images correlated with historical computed tomography scan data. Such a training dataset may be used to train shape identification model to generate a set of shape parameters representing a structure's shape as a function of a set of ultrasonic images, which may be input into the model in order to receive, as an output, a set of shape parameters. Shape identification model may be trained, by processor 104, using structure training data. Additionally, structure training data may include previously input image sets and their corresponding shape parameter outputs. Shape identification model may be iterative such that outputs may be used as future inputs of shape identification model. This may allow the shape identification model to evolve. Processor 104 may be further configured to generate set of shape parameters as a function of plurality of ultrasonic images 124 using the trained shape identification model.

Still referring to FIG. 1, generating a set of shape parameters may include performing image processing/segmentation techniques, as described above, prior to implementation of shape identification model in order to optimize performance and runtime of processor 104 and training of model. For example, image segmentation may include normalization and standardization methods performed by computer vision model to ensure that pixel values in ultrasonic images are normalized or standardized to a consistent scale thus aiding convergence during training of shape identification model. Image segmentation may include data augmentation techniques such as rotation, scaling, flipping, and translation to artificially increase the size of the training dataset and improve model generalization. Image segmentation may include image enhancement preprocessing techniques like histogram equalization or contrast stretching to enhance relevant features in the images. Image segmentation may include texture and shape descriptors to extract features beyond pixel values, such as texture and shape descriptors, to capture additional information about structures. Image segmentation may include architecture selection methods, as in experiments with different architectures, such as U-Net, DeepLab, or custom architectures, depending on the complexity and characteristics of the images. Image segmentation may include grid Search or random Search processing methods to systematically explore hyperparameter combinations to find the optimal configuration for a 3D model. As previously disclosed, image segmentation may include separating specific structures or regions of interest (ROI) from the background or other structures in a given ultrasonic image, wherein a collection of ROIs may be also incorporated by the shape parameter training data/structure training data.

Still referring to FIG. 1, processor 104 may use a statistical shape model to generate and/or iteratively refine a 3D cardiac model 128 based on a set of shape parameters. In some cases, 3D cardiac model 128 may be generated through a direct 3D reconstruction from a series of (2D) ultrasonic images. In a non-limiting example, plurality of ultrasonic images 124 may include a plurality of ultrasonic images captured from different angles and positions within and/or around a structure. Processor 104 may be configured to apply one or more 3D reconstruction algorithms, such as without limitation, marching cubes, contour detection and segmentation, active contour models, and/or the like to create a coherent 3D representation e.g., 3D cardiac model 128 of a heart. In some cases, such direct 3D reconstruction may leverage the inherent spatial information within plurality of ultrasonic images 124, providing a direct and intuitive way to model 3D cardiac model 128. In a further embodiment, 3D modeling techniques may be applied to create the initial 3D model, such as surface modeling, solid modeling, or parametric modeling, among others. As an ordinary person skilled in the art, upon reviewing the entirety of this disclosure, will be aware of various 3D reconstruction algorithms that may be used by processor 104 to generate 3D cardiac model 128. As used in this disclosure, a "statistical shape model" (SSM) is a data structure representing, including, and/or utilizing a mathematical model that captures principal modes of variation in shape across a population of structures. In some cases, SSM may be constructed by analyzing one or more datasets of shapes and identifying, for example, mean shapes and main modes of variation within the one or more datasets. In a non-limiting example, SSM may start with calculation of at least one mean shape, which represents an average geometry of all shapes of a structure in a given dataset, wherein the at least one mean shape may be served as a central reference point for processor 104 to understand different variations. In some embodiments, unique SSMs are created for different structure categories, such as different organs or tissues. In a non-limiting example, a first SSM may be created for a first structure category such as kidneys and a second SSM may be created for a second structure category such as hearts. In some cases, dataset may include, without limitation, structure training data, and/or datasets within ultrasonic image databases described herein. SSM may also identify one or more principal modes of variation within given datasets described herein, wherein the "principal modes of variations," for the purpose of this disclosure, refer to main patterns or directions along which data points vary within dataset. In a non-limiting example, identifying principal modes of variations may include applying principal component analysis (PCA) on given dataset. Additionally, or alternatively, shapes may be described directly using plurality of shape parameter sets (in structure training data). In some cases, shape parameter sets may correspond to a plurality of modes of variations. Further, one or more statistical constraints (e.g., mean, variance, correlation, boundary, proportion constraint and/or the like) may be introduced into SSM based on the distribution of shape parameters within plurality of shape parameter sets and/or 3D structure dimensions. In some embodiments, each shape parameter within a set of shape parameters may be associated with and/or comprise a corresponding parameter range. Such a parameter range may, for example, include a range of values associated with a normal and/or healthy heart. Such a parameter range may be determined based on, for example, a subset of possible values of a parameter which historical healthy structures commonly fall into, as determined from a dataset.

Still referring to FIG. 1, in some cases, once modes of variation are extracted, processor 104 may be configured to create a shape representation for any given structure shape within the studied class. In a non-limiting example, 3D cardiac model 128 having a shape S may be mathematically represented as $$S = \overline{S} + \sum_{k=1}^{M} a_k \times \phi_k,$$

wherein $\overline{S}$ denotes the mean shape derived from the set of example shapes, M is the number of modes of variation considered, $a_k$ are the coefficients or weights for each mode, and $\phi_k$ are the modes of variation (eigenvectors corresponding to the kth principal component). In some cases, coefficients $a_k$ may dictate a degree to which each mode of variation is present in shape S. In some cases, coefficients $a_k$ may vary from positive to negative (or negative to positive) based on the deformation of the 3D cardiac model 128 in directions described by each mode of variation. In some cases, 3D cardiac model 128 may include mean shape as described herein. In some cases, 3D cardiac model 128 may include a predictive structure shape that may not have been explicitly seen in the set of example shapes or patient's heart observations. In some cases, 3D cardiac model 128 may be in 3D VOR as described above.

Still referring to FIG. 1, generating the 3D cardiac model 128 may include transforming 3D cardiac model 128 to a second model as a function of a plurality of mode changers within SSM, wherein each mode changer of the plurality of mode changers is associated with a model feature of 3D cardiac model 128. As used in this disclosure, a "mode changer" is an algorithmic component derived from PCA configured to encapsulate a specific mode of variation as described above (representing a distinct way in which the shape of 3D cardiac model 128 may deviate from the mean shape). A "model feature," for the purpose of this disclosure, is a distinct, recognizable and quantifiable attribute or characteristic of the 3D cardiac model 128. For example, and without limitation, model feature may include an anatomical feature such as the size and curvature of the ventricles, the thickness of the heart wall, the positioning of heart valves or the like. In some cases, model feature may correspond to at least one shape parameter as described herein. In a non-limiting example, a mode changer may be associated with the size variation of the left ventricle identified within 3D cardiac model 128. Such mode changer may be adjusted to modify the volume of the left ventricle, resulting in a second 3D model that mimics potential biological variations or specific patient conditions that is different from original 3D cardiac model 128. In some cases, multiple mode changers of SSM may be adjusted simultaneously. For example, and without limitation, the rigid registration might involve translations and rotations to superimpose the shapes; affine registration could incorporate scaling, shearing, and other linear transformations; while non-rigid methods might employ B-splines, thin-plate splines, or diffcomorphic transformations to flexibly map one shape onto another. In some cases, an averaged position of each corresponding point (or voxel) across all example shapes may be calculated using formula $$\overline{p}_i = \frac{1}{N} \sum_{j=1}^{N} p_{ji},$$

where $\overline{p}_i$ is the mean position of the ith point (or voxel), $p_{ji}$ is the position of the ith point in the jth example shape, and N is the total number of example shapes in the labeled set.

In some cases, principle component analysis (PCA) may be applied to the aligned shapes to extract at least a primary mode of variation. As described herein, a "primary mode of variation" is a mode of variation that have the most significant variability, wherein the "mode of variation," for the purpose of this disclosure, is a specific pattern or direction of a shape change. In some cases, such significancy may be indicated by the first principal component in PCA. In some cases, a plurality of modes of variation may be extracted, wherein each mode (or principal component) may represent a specific way the shape of structure may be deformed from the mean shape, determined by one or more eigenvectors of the covariance matrix of the aligned shapes. In a non-limiting example, eigenvector with the highest eigenvalue may represent primary mode of variation which captures the largest amount of shape variability within example shapes, while subsequent modes (eigenvectors) capture decreasing amounts of variability. In a non-limiting example, a feature and/or component of apparatus 100, may be consistent with any feature and/or component disclosed in PCT App. Ser. No. PCT/US24/47990, filed on Sep. 23, 2024, and entitled "APPARATUS AND METHODS FOR GENERATING A THREE-DIMENSIONAL (3D) MODEL OF AN ANATOMICAL OBJECT VIA MACHINE-LEARNING," U.S. patent application Ser. No. 18/376,688, filed on Oct. 4, 2023, and entitled "APPARATUS AND METHODS FOR GENERATING A THREE-DIMENSIONAL (3D) MODEL OF CARDIAC ANATOMY VIA MACHINE-LEARNING," U.S. patent application Ser. No. 18/750,411, filed on Jun. 21, 2024, and entitled "APPARATUS AND METHODS FOR GENERATING A THREE-DIMENSIONAL (3D) MODEL OF CARDIAC ANATOMY VIA MACHINE-LEARNING," U.S. patent application Ser. No. 18/389,513, filed on Nov. 14, 2023, and entitled "APPARATUS AND METHODS FOR SYNTHETIZING MEDICAL IMAGES," U.S. patent application Ser. No. 18/426,604, filed on Jan. 30, 2024, and entitled "APPARATUS AND METHOD FOR GENERATING A THREE-DIMENSIONAL (3D) MODEL OF CARDIAC ANATOMY BASED ON MODEL UNCERTAINTY," U.S. patent application Ser. No. 18/648,176, filed on Apr. 26, 2024, and entitled "APPARATUS AND METHODS FOR VISUALIZATION WITHIN A THREE-DIMENSIONAL MODEL USING NEURAL NETWORKS," each of which is incorporated herein by reference in its entirety.

Still referring to FIG. 1, in some embodiments, apparatus 100 may determine cardiac measurement 148 based on 3D cardiac model 128. As used herein, a "cardiac measurement" is a quantitative value representing a physical characteristic of a heart. In some embodiments, a cardiac measurement may include an ostial diameter. In some embodiments, a cardiac measurement may include an ostial length. In some embodiments, a cardiac implant size 152 may be determined based on a cardiac measurement 148, such as a maximum ostial size. In some embodiments, a cardiac implant size 152 may be determined based on 3D cardiac model 128. A "cardiac implant size," for the purposes of this disclosure, is a datum or data representing at least a dimension of a cardiac implant. A cardiac implant size may include a left atrial appendage occlusion device size. A cardiac implant size may include a Watchman device size.

Still referring to FIG. 1, In some embodiments, a cardiac implant placement 156 may be determined based on a cardiac measurement 148 and/or 3D cardiac model 128. As used herein, a "cardiac implant placement" is a location of a cardiac implant, a location of a component of a cardiac implant, or both. In some embodiments, a cardiac implant placement may include a placement of a Watchman device.

In some embodiments, a cardiac implant candidate quality 160 may be determined based on a cardiac measurement 148 and/or 3D cardiac model 128. As used herein, a "cardiac implant candidate quality" is a measure of whether a subject is a suitable candidate for receiving a cardiac implant, the degree to which a subject is a suitable candidate for receiving a cardiac implant, or both. In some embodiments, a cardiac implant candidate quality 160 may include a measure of whether a subject is a suitable candidate for receiving a Watchman device and/or a measure of the degree to which a subject is a suitable candidate for receiving a Watchman device. In some embodiments, a candidate's suitability may be determined based on whether a thrombus is detected. As used herein, a "thrombus" is a blood clot formed in situ within the vascular system of a subject, where the blood clot impedes blood flow. In some embodiments, a thrombus machine learning model may be used to detect a thrombus based on plurality of ultrasonic images 124. In some embodiments, a thrombus machine learning model may detect one or more features within one or more images of plurality of ultrasonic images 124 and may determine a presence and/or absence of a thrombus based on such features. Such features may include, as non-limiting examples, irregularity of edges, shapes of structures detected within an image, mean intensity and/or standard deviation of intensity of a region. In some embodiments, thrombus machine-learning model may be trained on training data correlating ultrasonic images to labeled ultrasonic images. In some embodiments, labeled ultrasonic images may indicate the presence or absence of a thrombus. In some embodiments, labeled ultrasonic images may indicate a location of a thrombus. For example, irregularity of edges may indicate that a structure includes a thrombus, which may have less regular edges than healthy vessel walls. In another example, a shape of a structure and/or a degree to which a structure has a circular or irregular shape may be used to distinguish a thrombus (which may have an irregular shape) from a healthy blood vessel (which may have a circular cross section).

Still referring to FIG. 1, apparatus 100 may include a display device. As used in this disclosure, a "display device" is an electronic device that visually presents information to a user. In an embodiment, display device may include a user interface that translates data such as, without limitation, cardiac measurement 148, 3D cardiac model 128, cardiac implant size 152, cardiac implant placement 156, and cardiac implant candidate quality 160. A user interface may include a graphical user interface (GUI), wherein the GUI may include a window in which data described herein may be displayed. In an embodiment, a user interface may include one or more graphical locator and/or cursor facilities allowing user to interact with cardiac measurement 148, 3D cardiac model 128, cardiac implant size 152, cardiac implant placement 156, and cardiac implant candidate quality 160, for instance, by using a touchscreen, touchpad, mouse, keyboard, and/or other manual data entry device. In some cases, 3D cardiac model 128 may be interactive. For instance, medical professionals may rotate, zoom, and/or explore 3D cardiac model 128 from various angles. A user may enter user input containing selecting specific regions, adding comments, adjusting parameter, and the like. In a non-limiting example, user interface may include one or more menus and/or panels permitting selection of measurements, models, visualization of data/model to be displayed and/or used, elements of data, functions, or other aspects of data/model to be edited, added, and/or manipulated, options for importation of and/or linking to application programmer interfaces (APIs), exterior services, data source, machine-learning models, and/or algorithms, or the like. Persons skilled in the art, upon reviewing the entirety of this disclosure, will be aware of various ways in which a visual interface and/or elements thereof may be implemented and/or used as described in this disclosure.

Still referring to FIG. 1, in some embodiments, a computing device may determine a Left Atrial Appendage Occlusion Device placement as a function of 3D cardiac model 128. In some embodiments, a computing device may determine a size of a Left Atrial Appendage Occlusion Device placement as a function of 3D cardiac model 128. In some embodiments, a computing device may determine whether there is leakage resulting from Left Atrial Appendage Occlusion Device placement as a function of 3D cardiac model 128. In some embodiments, a determined Left Atrial Appendage Occlusion Device size, placement, and/or leakage may be displayed to a user, such as by a display device.

Still referring to FIG. 1, in some embodiments, an apparatus and/or method described herein may allow ultrasonic imaging to replace and/or be an alternative to MRIs and/or CT scans. This may limit radiation exposure of subjects.

Still referring to FIG. 1, in some embodiments, use of a TEE sweep from multiple angles to recreate a 3D mesh of the left atrium anatomy may enable accurate measurement of maximal ostium diameters of the left atrial appendage (LAA) as needed for device sizing. This can help increase initial device size selection without necessitating any additional scanning or radiation exposure for patients. Improved device size selection may also result in lower number of devices per procedure and overall shorter procedure time. An apparatus or method described herein can further be used to guide transseptal puncture and navigation of a sheath and delivery system, helping case the implantation procedure itself.

Still referring to FIG. 1, measurement of the sizes from ICE views may be more subjective and not as clear as with TEE. This may increase the cognitive burden on the physician to arrive at the best view where the 'maximal' ostial diameter is visible while navigating the catheter across the septum and within the left atrium. Additionally, a TEE probe may be manipulated and measured by a sonographer, freeing up a physician to focus on appropriate delivery and placement.

Still referring to FIG. 1, 3D reconstruction of the LAA from ICE may aid workflows of physicians who wish to perform an implantation procedure without TEE, making it easier to obtain the 'maximal' measurements on the reconstructed 3D LA/LAA mesh instead of navigating an ICE catheter to the appropriate view.

Figure 2:
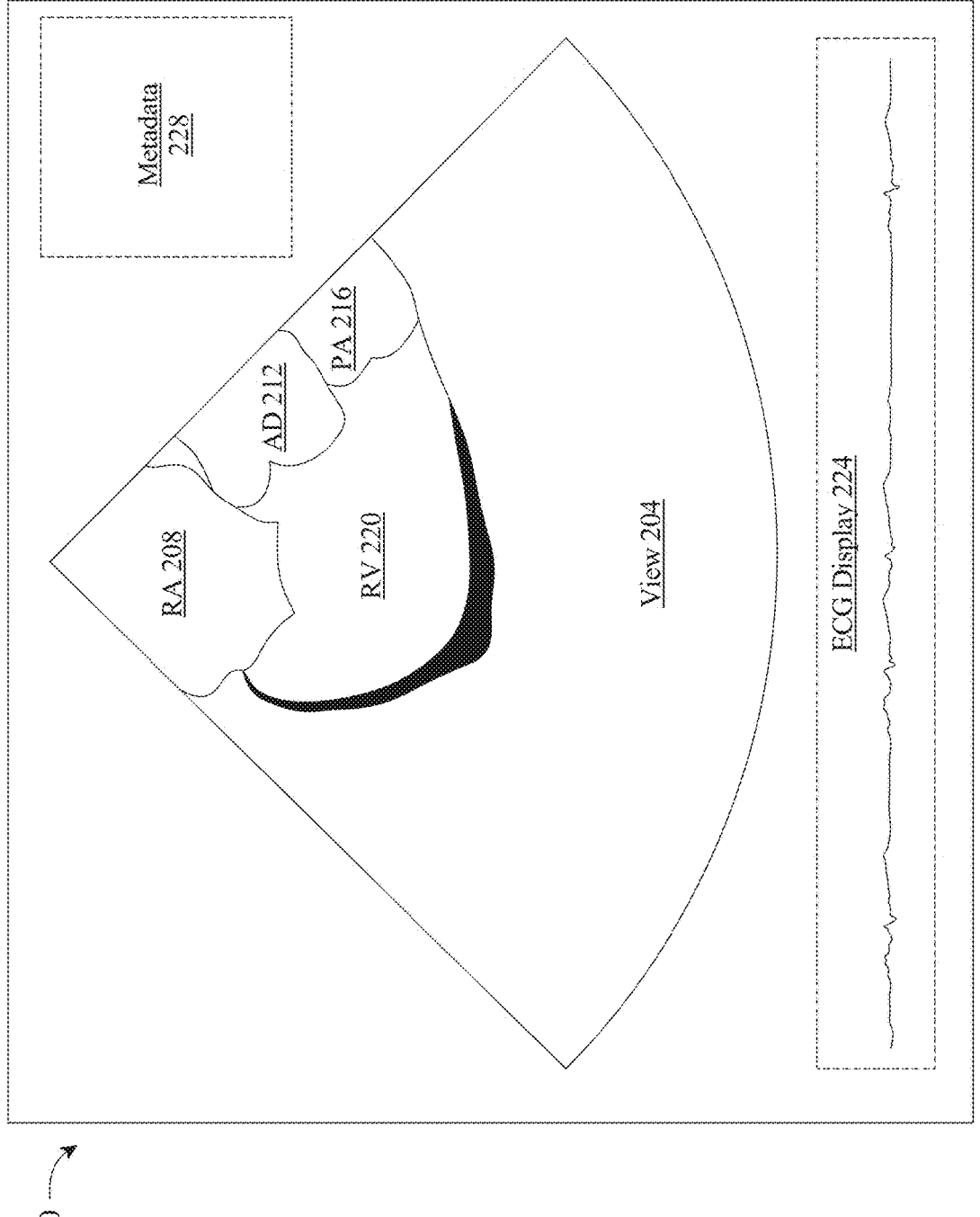
FIG. 2 shows an exemplary embodiment of an intracardiac echocardiography (ICE) image.

Now referring to FIG. 2, an exemplary embodiment of an ultrasonic image such as ICE image 200 is illustrated. As described above with reference to FIG. 1, plurality of ultrasonic images 124 may include a plurality of ICE images, wherein each ICE image of the plurality of ICE images is a specialized form of echocardiography that may provide detailed image of heart's interior structures. In a non-limiting example, plurality of ICE images may include an ICE video (e.g., plurality of ICE images arranged in a corresponding time sequence). In an embodiment, ICE image 200 may be real-time, dynamic ultrasound image that provide a (detailed) view 204 of heart's interior structures, including, without limitation, right atrium (RA) 208, anterior descending (AD) 212, pulmonary atresia (PA) 216, and right ventricular (RV) 220.

With continued reference to FIG. 2, in some cases, ICE image 200 may include gray scaled image. It should be noted that, in some cases, ICE image 200 may be configured to visualize blood flow and/or blood flow patterns within the heart via color doppler. In some cases, resolution and/or clarity of ICE image 200 as described herein may be superior to transthoracic or transesophageal echocardiography due to the ICE catheter may be positioned inside the heart, closer to the structures being imaged.

Still referring to FIG. 2, in a non-limiting example, heart chambers may appear as dark, anechoic (black) areas since they are filled with blood, which doesn't reflect ultrasound waves well. Heart walls, valves, and/or other structures may appear as varying shades of gray, depending on their density and composition, in some cases, Color Doppler overlays may show blood flow in different colors, indicating the direction and speed of blood flow. For instance, and without limitation, red may indicate flow towards the probe, while blue may indicate flow away from the probe.

With continued reference to FIG. 2, in a non-limiting embodiment, ICE image 200 may be synchronized with ECG data, allowing for precise timing of cardiac events with anatomical visualization provided by ICE. In some cases, ICE image 200 may include an ECG display 224 configured to display ECG waveform as a continuous line graph at the top, bottom, or side of ICE image 200. In some cases, specific parts of the cardiac cycle e.g., systole or diastole, may be correlated with visual data from ICE image 200.

Additionally, or alternatively, and still referring to FIG. 2, ICE image 200 may come with accompanying metadata 228 displayed on the side or corners of ICE image 200 as described herein. In some cases, metadata 228 may provide essential contextual information about ICE image 200 and/or the corresponding patient. In a non-limiting example, metadata 228 may include patient information (e.g., patient ID, name, DOB, age, gender, and the like), image acquisition details (e.g., date and time, probe type, frequency, depth, gain, and the like), procedure-related information (e.g., procedure name, operator, location, and the like), ECG trace (e.g., ECG data as described above), measurement annotations (e.g., any measurements taken directly on the image e.g., diameter, a value of thickness of a heart wall and the like), image sequence information (e.g., image number, total number of frames, and the like), comments or notes, hospital or clinic information, and/or the like. As an ordinary person skilled in the art, upon reviewing the entirety of this disclosure, will be aware of ICE image 200 and various components thereof may be incorporated by apparatus 100 for generating 3D model of cardiac anatomy.

Figure 3:
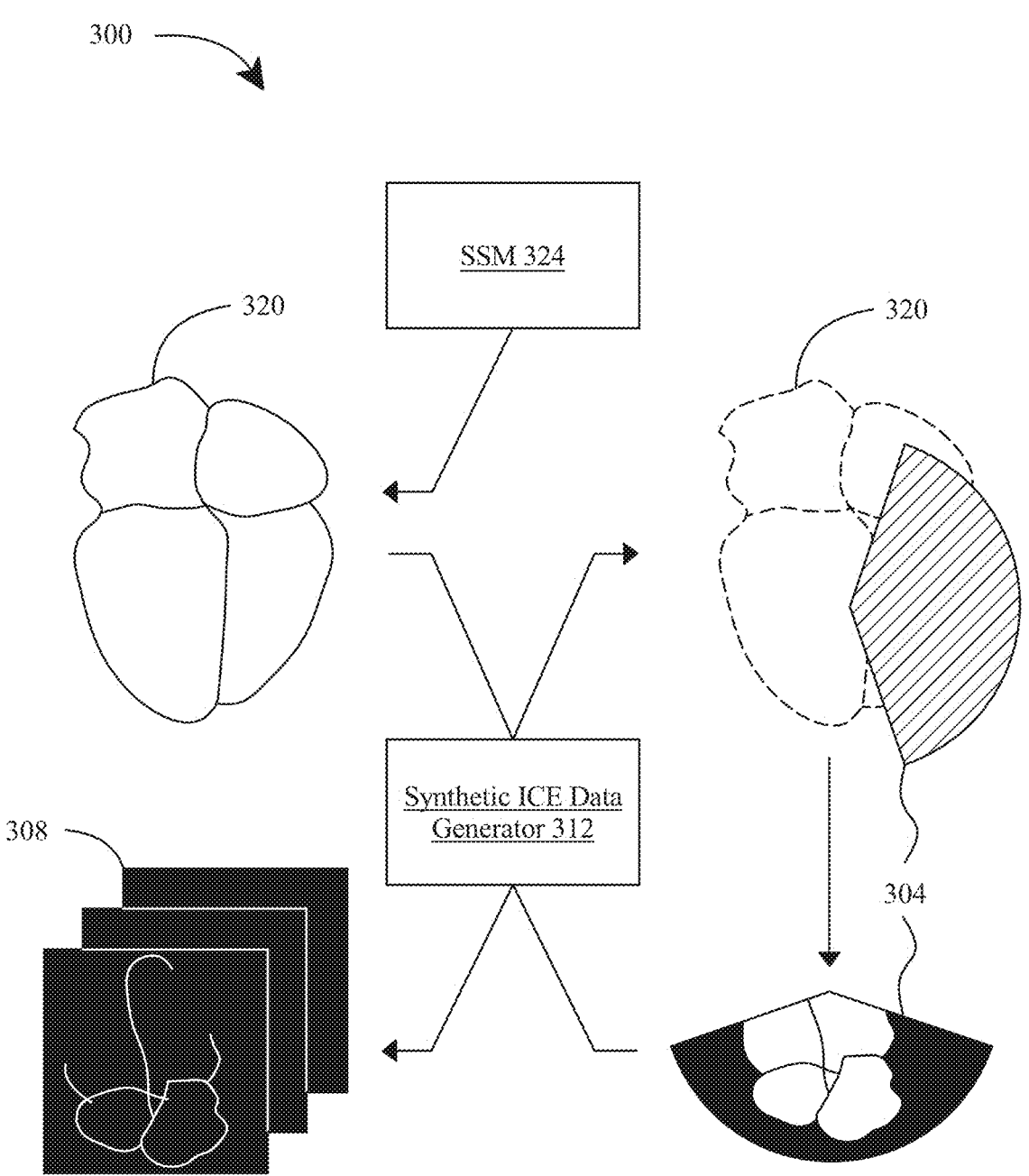
FIG. 3 is a flow diagram of an exemplary embodiment of an ICE image example generation process.

Now referring to FIG. 3, a flow diagram of an exemplary embodiment of an ultrasonic image such as ICE example generation process 300. In an embodiment, structure training data may be generated, at least in part, via ICE example generation process 300. In some cases, processor 104 may be configured to receive a 3D model of the heart, such as any 3D model of heart 320 as described herein and identify an ICE view 304 (i.e., visual representation of image obtained using intracardiac echocardiography as described above e.g., ICE image 200) based on the received 3D model. In some cases, 3D model received by processor 104 may be derived from CT scans as described above with reference to FIG. 1. In other cases, processor may receive CT scans directly instead of 3D models. A synthetic ICE frame 308 may then be generated, by processor 104, as a function of identified ICE view 304, wherein the synthetic ICE frame 308 may be used as one or the training examples in structure training data.

With continued reference to FIG. 3, in some cases, processor 104 may interface with one or more 3D models (i.e., detailed representation of heart's anatomy in a 3D space, capturing intricate structures, chambers, vessels, valves, among others) as described above, or other imaging modalities and/or databases, and equipped with algorithms e.g., CNN, gradient boosting machines, SVM, PCA, and/or the like to analyze model's geometry and spatial relationships upon receiving the 3D models. In some cases, 3D models may be received from SSM 324 as described above with reference to FIG. 1 via a communicative connection between processor 104 and SSM 324. In a non-limiting example, processor 104 may be configured to determine an optimal viewpoints or angles from which ICE view 304 would provide a desired diagnostic value or procedural guidance.

Still referring to FIG. 3, in some cases, identification and selection of ICE view 304 may be automatically identified, using one or more machine learning models as described herein. In a non-limiting example, processor 104 may utilize one or more machine learning models trained on cardiac anatomy viewpoints identification training data, wherein the cardiac anatomy viewpoints identification training data may include a plurality of cardiac anatomies as input correlated to a plurality of ICE images as output and identify at least one ICE view 304 (most informative) for a given cardiac anatomy using the trained machine learning models.

Still referring to FIG. 3, in other cases, ICE view 304 may be defined by a user such as a medical professional. In a non-limiting example user interface of display device may allow a user (e.g., a clinician) to manually rotate, pan, and zoom displayed 3D model and/or corresponding CT scans. As user do so, processor 104 may dynamically calculate and displays potential ICE views 304 based on user's chosen perspective. Additionally, or alternatively, depending on cardiac procedure being planned or executed, processor 104 may prioritize certain ICE views 304. For instance, and without limitation, ICE view 304 may be pre-defined. For atrial fibrillation ablation, ICE view 304 may showcase the pulmonary veins' entrances into the LA may be emphasized. In other cases, ICE view 304 may be automatically identified, by processor 104, using one or more machine learning models as described herein, such as, without limitation, synthetic ICE data generator as described in detail below.

With continued reference to FIG. 3, as used in this disclosure, a "synthetic ICE frame" refers to a digitally generated or simulated image that emulates a visual representation obtained from ICE view 304. In some cases, synthetic ICE frames 308 may be produced using computational methods and/or models such as, without limitation, a synthetic ICE data generator 312 based on pre-existing data, models, or simulations e.g., identified ICE views 304. In a non-limiting example, synthetic ICE frames 308 may include a simplified version e.g., an image illustrating heart anatomy via a plurality of lines indicating contours of heart's structure as shown in FIG. 3. One or more image processing techniques and/or computer vision algorithms such as, without limitation, histogram equalization, adaptive filtering, edge detection (e.g., Canny or Sobel operators), contour extraction, and/or the like may be applied, by processor 104, on a segmented CT scan and/or 3D models based on identified ICE view 304. Synthetic ICE frame 308 may be rendered on a blank canvas or background that mimics the echogenicity of an ICE image according to extracted contours, wherein the extracted contours may be represented as a bold lines and enhanced with shading to give depth. In some cases, synthetic ICE frame 308 may be validated and verified by overlaying synthetic ICE frame 308 onto original ICE view 304, ensuring accuracy and resemblance.

Still referring to FIG. 3, in some cases, generating synthetic ICE frames 308 may include implementations of one or more aspects of "generative artificial intelligence," a type of AI that uses machine learning algorithms to create, establish, or otherwise generate data. Such data may include, without limitation, ultrasonic image that is similar to one or more provided training examples. In an embodiment, machine learning module described herein may generate one or more generative machine learning models that are trained on one or more set of CT scans and/or 3D models in ICE image view 304 as described above. Synthetic ICE data generator 312 may include one or more generative machine learning models may be configured to generate new examples that are similar to the training data of the one or more generative machine learning models but are not exact replicas; for instance, and without limitation, data quality or attributes of the generated examples may bear a resemblance to the training data provided to one or more generative machine learning models, wherein the resemblance may pertain to underlying patterns, features, or structures found within the provided training data.

Still referring to FIG. 3, in some cases, generative machine learning models within synthetic ICE data generator may include one or more generative models. As described herein, "generative models" refers to statistical models of the joint probability distribution P(X, Y) on a given observable variable x, representing features or data that can be directly measured or observed (e.g. CT scans and/or 3D models derived from CT scans) and target variable y, representing the outcomes or labels that one or more generative models aims to predict or generate (e.g., synthetic ICE frames 308). In some cases, generative models may rely on Bayes theorem to find joint probability; for instance, and without limitation, Naïve Bayes classifiers may be employed by computing device to categorize input data such as, without limitation, CT scans and/or 3D models derived from CT scans into different views.

In a non-limiting example, and still referring to FIG. 3, one or more generative machine learning models may include one or more Naïve Bayes classifiers generated, by processor 104, using a Naïve bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A)\div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Processor 104 may then calculate a likelihood table by calculating probabilities of different data entries and classification labels. Processor 104 may utilize a naïve Bayes equation to calculate a posterior probability for each class. A class containing the highest posterior probability is the outcome of prediction.

Still referring to FIG. 3, although Naïve Bayes classifier may be primarily known as a probabilistic classification algorithm; however, it may also be considered a generative model described herein due to its capability of modeling the joint probability distribution P(X, Y) over observable variables X and target variable Y. In an embodiment, Naïve Bayes classifier may be configured to make an assumption that the features X are conditionally independent given class label Y, allowing generative model to estimate the joint distribution as $P(X, Y)=P(Y)\Pi iP(Xi|Y)$, wherein P(Y) may be the prior probability of the class, and $P(X_i|Y)$ is the conditional probability of each feature given the class. One or more generative machine learning models containing Naïve Bayes classifiers may be trained on labeled training data, estimating conditional probabilities $P(X_i|Y)$ and prior probabilities P(Y) for each class; for instance, and without limitation, using techniques such as Maximum Likelihood Estimation (MLE). One or more generative machine learning models containing Naïve Bayes classifiers may select a class label y according to prior distribution P(Y), and for each feature $X_i$, sample at least a value according to conditional distribution $P(X_i|y)$. Sampled feature values may then be combined to form one or more new data instance with selected class label y. In a non-limiting example, one or more generative machine learning models may include one or more Naïve Bayes classifiers to generate new examples of ICE images based on CT scans and/or 3D models derived from CT scans (e.g., identified ICE views 304), wherein the models may be trained using training data containing a plurality of features of input data as described herein and/or the like correlated to a plurality of ICE views.

Still referring to FIG. 3, in some cases, one or more generative machine learning models may include generative adversarial network (GAN). As used in this disclosure, a "generative adversarial network" is a type of artificial neural network with at least two sub models (e.g., neural networks), a generator, and a discriminator, that compete against each other in a process that ultimately results in the generator learning to generate new data samples, wherein the "generator" is a component of the GAN that learns to create hypothetical data by incorporating feedbacks from the "discriminator" configured to distinguish real data from the hypothetical data. In some cases, generator may learn to make discriminator classify its output as real. In an embodiment, discriminator may include a supervised machine learning model while generator may include an unsupervised machine learning model as described in further detail with reference to FIGS. 6-8.

With continued reference to FIG. 3, in an embodiment, discriminator may include one or more discriminative models, i.e., models of conditional probability P(Y|X=x) of target variable Y, given observed variable X. In an embodiment, discriminative models may learn boundaries between classes or labels in given training data. In a non-limiting example, discriminator may include one or more classifiers as described in further detail below with reference to FIG. 6 to distinguish between different categories e.g., real vs. fake, or states e.g., TRUE vs. FALSE within the context of generated data such as, without limitations, synthetic ICE frames 308, and/or the like. In some cases, processor 104 may implement one or more classification algorithms such as, without limitation, Support Vector Machines (SVM), Logistic Regression, Decision Trees, and/or the like to define decision boundaries.

In a non-limiting example, and still referring to FIG. 3, generator of GAN may be responsible for creating synthetic data that resembles real ICE images. In some cases, GAN may be configured to receive CT scans and/or 3D models derived from CT scans as input and generates corresponding examples of ICE images containing information describing anatomy in different ICE views. On the other hand, discriminator of GAN may evaluate the authenticity of the generated content by comparing it to true ICE images, for example, discriminator may distinguish between genuine and generated content and providing feedback to generator to improve the model performance. Additionally, or alternatively, GAN may include a conditional GAN as an extension of the basic GAN as described herein that allows for generation of ICE images using pre-existing CT scans and/or 3D models derived from CT scans based on certain conditions or labels. In standard GAN, generator may produce samples from random noise, while in a conditional GAN, generator may produce samples based on random noise and a given condition or label.

With continued reference to FIG. 3, in other embodiments, one or more generative models may also include a variational autoencoder (VAE). As used in this disclosure, a "variational autoencoder" is an autoencoder (i.e., an artificial neural network architecture) whose encoding distribution is regularized during the model training process in order to ensure that its latent space includes desired properties allowing new data sample generation. In an embodiment, VAE may include a prior and noise distribution respectively, trained using expectation-maximization meta-algorithms such as, without limitation, probabilistic PCA, sparse coding, among others. In a non-limiting example, VEA may use a neural network as an amortized approach to jointly optimize across input data and output a plurality of parameters for corresponding variational distribution as it maps from a known input space to a low-dimensional latent space. Additionally, or alternatively, VAE may include a second neural network, for example, and without limitation, a decoder, wherein the "decoder" is configured to map from the latent space to the input space.

In a non-limiting example, and still referring to FIG. 3, VAE may be used by processor 104 to model complex relationships between CT scans and/or 3D models derived from CT scans. In some cases, VAE may encode input data into a latent space, capturing example ICE images. Such encoding process may include learning one or more probabilistic mappings from observed CT scans and/or 3D models derived from CT scans to a lower-dimensional latent representation. Latent representation may then be decoded back into the original data space, therefore reconstructing the 3D models representing example ICE images. In some cases, such decoding process may allow VAE to generate new examples or variations that are consistent with the learned distributions.

Additionally, or alternatively, and still referring to FIG. 3, processor 104 may be configured to continuously monitor synthetic ICE data generator. In an embodiment, processor 104 may configure discriminator to provide ongoing feedback and further corrections as needed to subsequent input data. An iterative feedback loop may be created as processor 104 continuously receive real-time data, identify errors (e.g., distance between synthetic ICE frame 308 and real ICE images) as a function of real-time data, delivering corrections based on the identified errors, and monitoring subsequent model outputs and/or user feedbacks on the delivered corrections. In an embodiment, processor 104 may be configured to retrain one or more generative machine learning models within synthetic ICE data generator based on user modified ICE frames or update training data of one or more generative machine learning models within synthetic ICE data generator by integrating validated synthetic ICE frames (i.e., subsequent model output) into the original training data. In such embodiment, iterative feedback loop may allow synthetic ICE data generator to adapt to the user's needs and performance requirements, enabling one or more generative machine learning models described herein to learn and update based on user responses and generated feedbacks.

With continued reference to FIG. 3, other exemplary embodiments of generative machine learning models may include, without limitation, long short-term memory networks (LSTMs), (generative pre-trained) transformer (GPT) models, mixture density networks (MDN), and/or the like. As an ordinary person skilled in the art, upon reviewing the entirety of this disclosure, will be aware of various generative machine learning models that may be used generating synthetic ICE frames 308.

Still referring to FIG. 3, in a further non-limiting embodiment, synthetic ICE data generator 312 may be further configured to generate a multi-model neural network that combines various neural network architectures described herein. In a non-limiting example, multi-model neural network may combine LSTM for time-series analysis with GPT models for natural language processing. Such fusion may be applied by computing device to generate synthetic ICE frames 308. In some cases, multi-model neural network may also include a hierarchical multi-model neural network, wherein the hierarchical multi-model neural network may involve a plurality of layers of integration; for instance, and without limitation, different models may be combined at various stages of the network. Convolutional neural network (CNN) may be used for image feature extraction, followed by LSTMs for sequential pattern recognition, and a MDN at the end for probabilistic modeling. Other exemplary embodiments of multi-model neural network may include, without limitation, ensemble-based multi-model neural network, cross-modal fusion, adaptive multi-model network, among others. As an ordinary person skilled in the art, upon reviewing the entirety of this disclosure, will be aware of various generative machine learning models that may be used to generating synthetic ICE frames 308 as described herein. As an ordinary person skilled in the art, upon reviewing the entirety of this disclosure, will be aware of various multi-model neural network and combination thereof that may be implemented by apparatus 100 in consistent with this disclosure.

Figure 4:
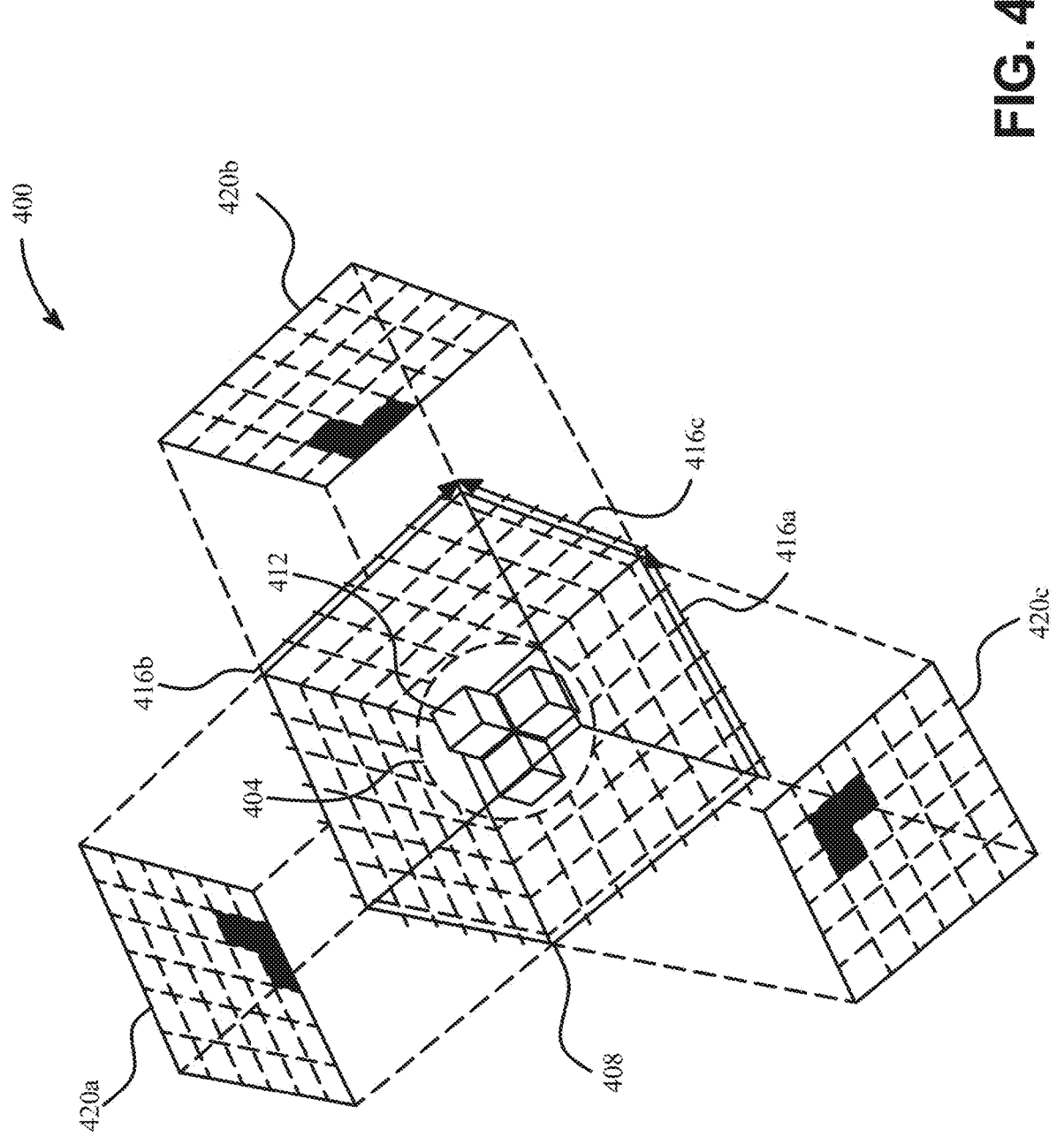
FIG. 4 illustrates an exemplary embodiment of a three-dimensional (3D) voxel occupancy representation.

Now referring to FIG. 4, an exemplary embodiment of a 3D VOR 400 is illustrated. 3D VOR 400 may be used to represent 3D object 404. In an embodiment, 3D VOR 400 may divide a 3D space 408 into a grid of one or more cubic units e.g., voxels 412, wherein each voxel 412 represents a specific volume within 3D space 408. In a non-limiting example, 3D object 404 may include a structure pertaining to a subject.

Still referring to FIG. 4, in some cases, each voxel 412 may act as a basic building block. In a non-limiting example, each voxel 412 may be configured to represent a discrete portion of 3D space 408. In an embodiment, each voxel 412 may include a presence indicator as described above with reference to FIG. 1, which denotes whether the voxel is occupied or unoccupied. In such embodiment, the binary or continuous value may allow 3D VOR 400 to map the presence or absence of material within each voxel 412, creating a granular representation of 3D object 404.

With continued reference to FIG. 4, in some cases, the resolution of 3D VOR 400 may be determined by the size and number of voxels within the grid. In a non-limiting example, smaller voxel may provide a higher resolution, capturing finer details, while larger voxels offer a more generalized representation.

Still referring to FIG. 4, in an embodiment, voxels 412 may be arranged in a regular pattern along three axis 416*a-c*, each pointing a distinct direction. In a non-limiting example, voxels 412 may be arranged along x, y, and z axes, wherein such arrangement may facilitate efficient manipulation and rendering of the 3D object 404. In some cases, spatial features 420*a-c* such as, without limitation, edges, surfaces, textures, and any other spatial features as described above with reference to FIG. 1, may be extracted from 3D VOR 400 by analyzing the relationships and patterns between neighboring voxels.

Figure 5:
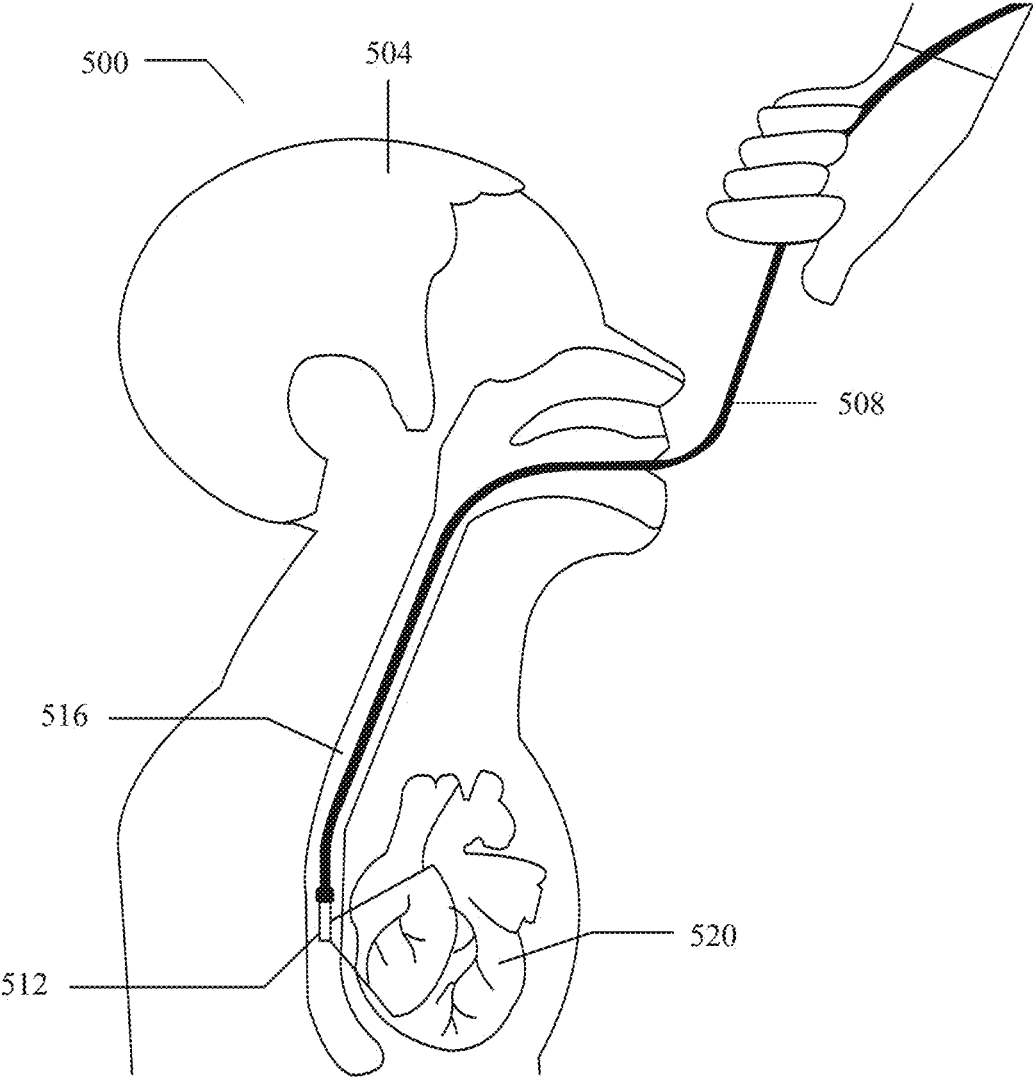
FIG. 5 is a schematic diagram of an exemplary transesophageal echocardiogram.

Now referring to FIG. 5, a schematic of an exemplary transesophageal echocardiogram (TEE) procedure 500 is shown. In some cases, TEE 500 may be performed during another procedure for instance heart surgery. According to some embodiments, a patient 504 has an endoscope 508, with an ultrasonic transducer 512, inserted into his esophagus 516. As one's esophagus 516 is proximal one's heart 520, ultrasonic transducer 512 may generate echocardiograms.

Still referring to FIG. 5, in some embodiments, transesophageal echocardiography (TEE) may provide superior imaging quality than intracardiac echocardiography (ICE), as larger ultrasound transducers 512 may be placed within the esophagus 516 than within heart 520. In some cases, ultrasound transducers must be substantially miniaturized to fit within heart 520, as in ICE catheters. As esophagus 516 may be proximal to heart 520, TEE may provide a clear image of various heart structures without needing vascular access (as commonly required by ICE). Additionally, TEE may be performed without obstructing patient's 504 ribcage and intermediary tissues (as commonly required by transthoracic echocardiography [TTE]). In some cases, TEE images may also provide information associated with angle of acquisition. Angle of acquisition may be an angle of TEE probe with respect to esophagus 516 (e.g., esophageal axis).

Figure 6:
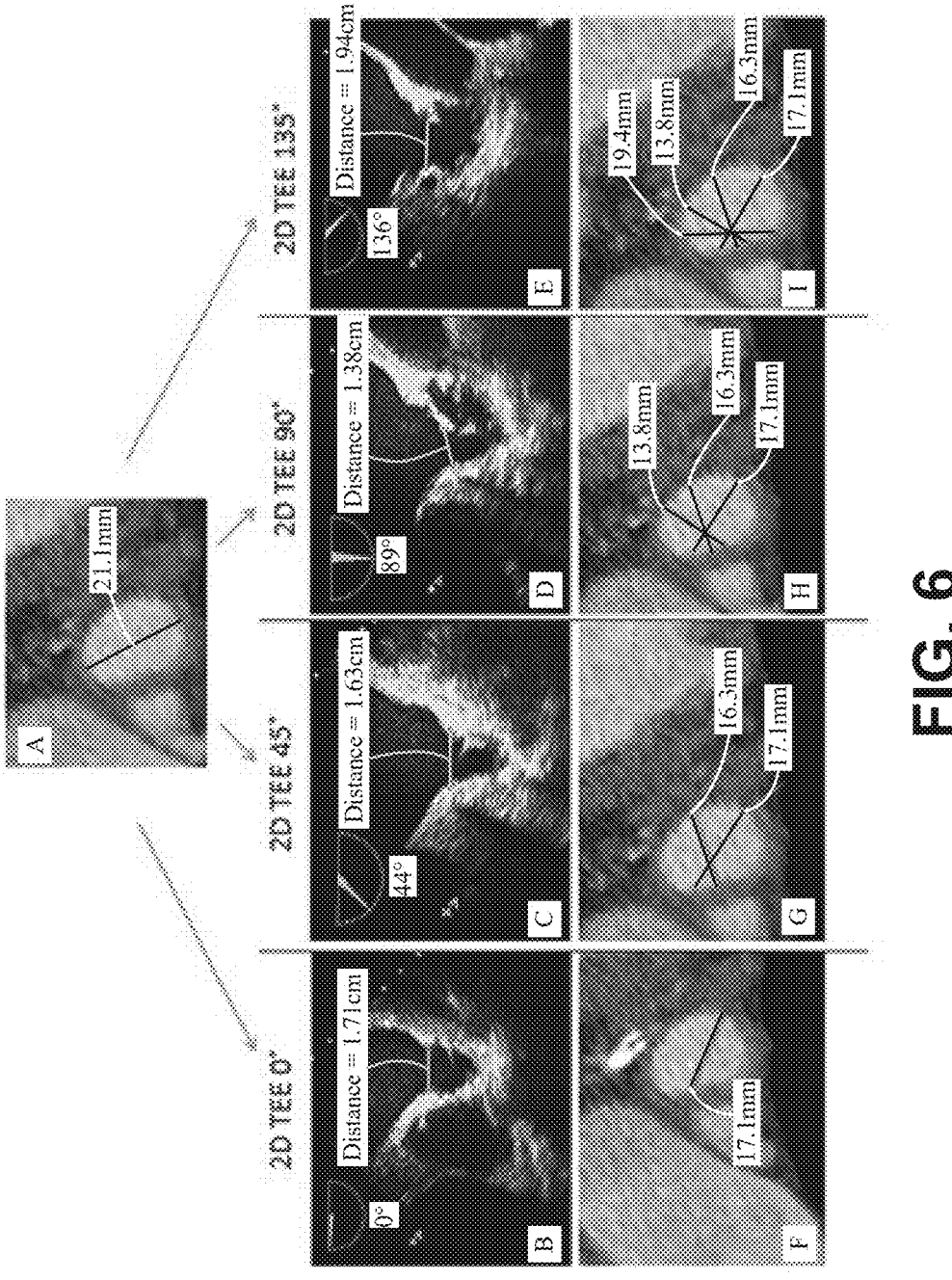
FIG. 6 presents 2D transesophageal echocardiogram (TEE) views at varying orientations.
Figure 7:
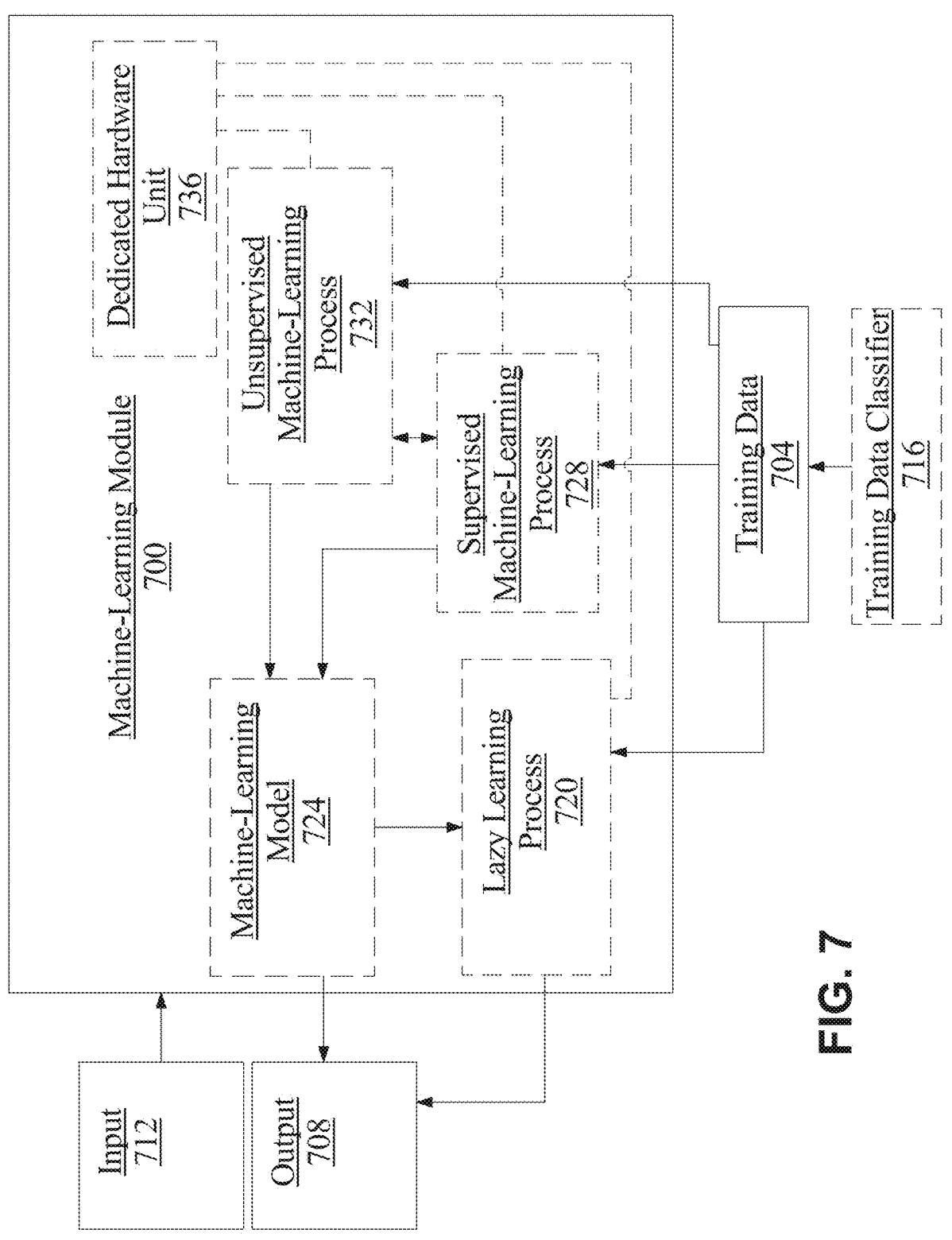
FIG. 7 is a block diagram of an exemplary embodiment of a machine learning model.
Figure 8:
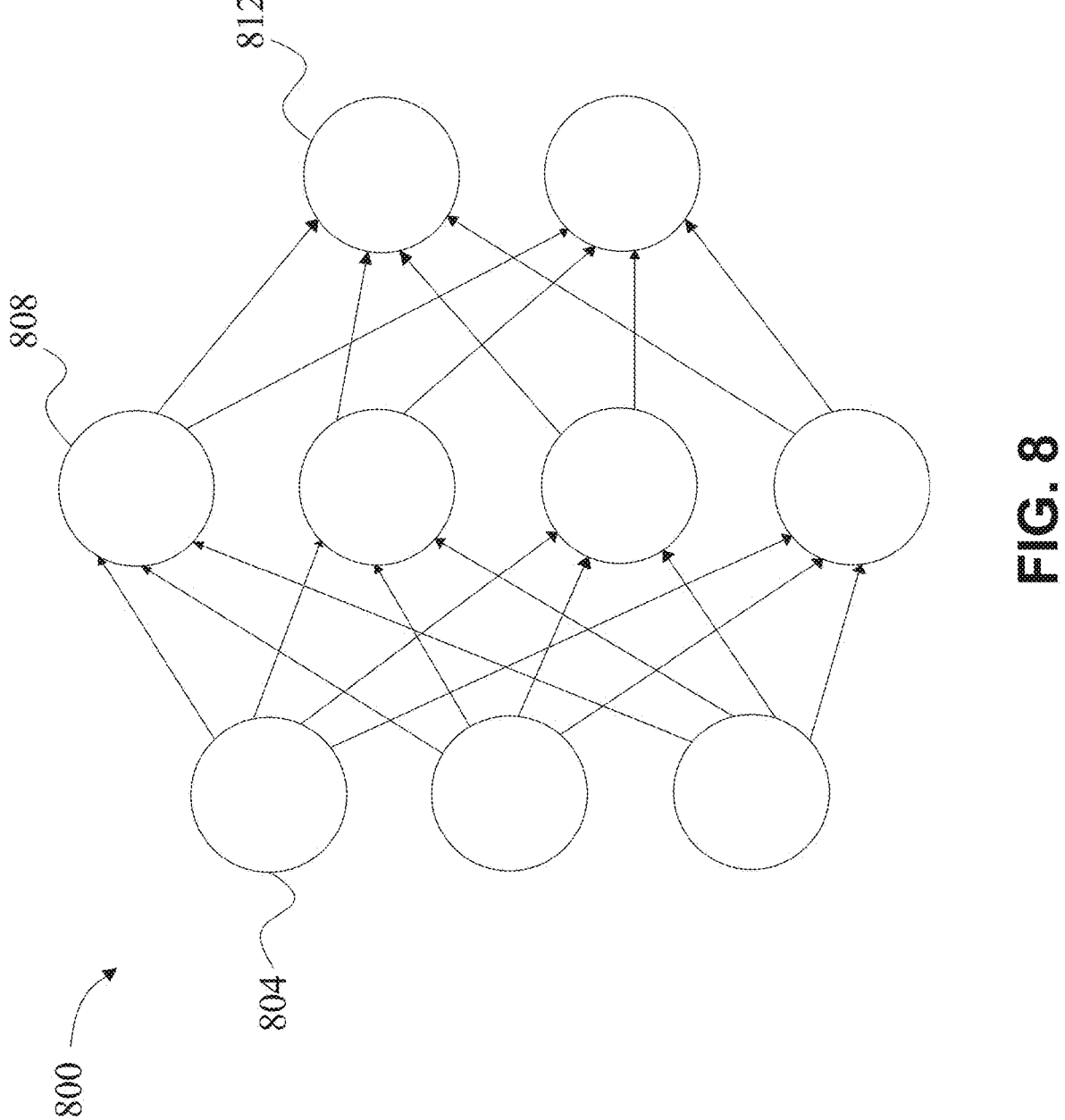
FIG. 8 is a schematic diagram of an exemplary embodiment of a neural network.

Still referring to FIG. 5, in some embodiments, TEE echocardiogram data, including images showing heart structures and, in some cases, angle of acquisition, may be used as input to any machine learning process described in this application, for instance with reference to FIGS. 6-8. For instance TEE echocardiogram data may be used to reconstruct 3D heart models. In some cases, TEE echocardiogram data is input into a machine learning model that outputs a 3D heart model (e.g., 3D mesh model and/or statistical shape model).

Still referring to FIG. 5, in some embodiments, TEE may be a preferred imaging modality for structural heart interventions, such as without limitation left atrial appendage occlusion (LAOO) and aortic/mitral/other heart valve replacement procedures. In some cases, technology and improvements described in this disclosure permit creation and/or modification of a 3D heart mesh from TEE data to aid in planning implant size selection, as well as to guide implantation procedures. In some cases, virtual placement of a 3D model of a candidate implant (such as without limitation LAAO device and/or heart valve implants) can be simulated on a 3D heart model generated by any method described in this disclosure. This novel and improved functionality may validate appropriate size and placement of implants within heart 520, as well as other organs within body of patient 504. For example, in the context of electrophysiology procedures, TEE 500 can be used to create heart anatomical models that can be used as reference for electroanatomic mapping, and guidance of ablation catheters for atrial fibrillation procedures (such as without limitation pulmonary vein isolation).

Still referring to FIG. 5, in some embodiments, applications described with reference to TEE 500 above can be extended for use with TTE and point of care ultrasound (POCUS). In some cases, both TTE and POCUS may acquire ultrasound images of chest/surface of patient 504. In some cases, TTE and POCUS data may be used as an input (and/or training data) for any machine learning process described in this disclosure, for instance with reference to FIGS. 6-8. In some cases, use of TTE and/or POCUS data (in machine learning processes described in this disclosure) may require adjustment in ultrasound acquisition parameters and positions to acquire a sufficient number of frames for 3D reconstruction. In some cases, TTE and POCUS offer improved accessibility (with POCUS being portable/mobile as well) and non-invasive 3D heart modeling, often without anesthesia or sedation, compared to catheterized 3D heart modeling commonly performed today for electroanatomical mapping and ablation procedures.

Referring now to FIG. 6, multiple 2D transesophageal echocardiogram (TEE) views at varying orientations are presented. Image A demonstrates a maximal LAA diameter of 21.1 mm obtained utilizing the double-oblique multiplanar reconstruction methodology by 3D CT. Panels B-E demonstrate the traditional 2D TEE LAA scanning views of 0°, 45°, 90°, and 135° views reflected on a multiplanar reconstruction of the LAA ostium on 3D CT. In panels F-I, the CT dimensions are taken at a focal intersection point and angled, from 0° (assigned as the measurement of 17.1 mm), and increased by 45° around this focal point for each subsequent measurement. Panel I demonstrate in this patient the 135° TEE measurement of 19.4 mm as off-axis to the true centroid of the LAA, and is not reflective of the maximal LAA width as shown in panel A, thereby resulting in an undersized WATCHMAN device. By CT, this patient would receive a 24 mm device with no peri-watchman leak.

Referring now to FIG. 7, an exemplary embodiment of a machine-learning module 700 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 704 to generate an algorithm instantiated in hardware or software logic, data structures, and/or functions that will be performed by a computing device/module to produce outputs 708 given data provided as inputs 712; this is in contrast to a non-machine learning software program where the commands to be executed are determined in advance by a user and written in a programming language.

Still referring to FIG. 7, "training data," as used herein, is data containing correlations that a machine-learning process may use to model relationships between two or more categories of data elements. For instance, and without limitation, training data 704 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 704 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 704 according to various correlations; correlations may indicate causative and/or predictive links between categories of data elements, which may be modeled as relationships such as mathematical relationships by machine-learning processes as described in further detail below. Training data 704 may be formatted and/or organized by categories of data elements, for instance by associating data elements with one or more descriptors corresponding to categories of data elements. As a non-limiting example, training data 704 may include data entered in standardized forms by persons or processes, such that entry of a given data element in a given field in a form may be mapped to one or more descriptors of categories. Elements in training data 704 may be linked to descriptors of categories by tags, tokens, or other data elements; for instance, and without limitation, training data 704 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 7, training data 704 may include one or more elements that are not categorized; that is, training data 704 may not be formatted or contain descriptors for some elements of data. Machine-learning algorithms and/or other processes may sort training data 704 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 704 to be made applicable for two or more distinct machine-learning algorithms as described in further detail below. Training data 704 used by machine-learning module 700 may correlate any input data as described in this disclosure to any output data as described in this disclosure. As a non-limiting illustrative example inputs may include ultrasonic image data and outputs may include 3D cardiac models.

Further referring to FIG. 7, training data may be filtered, sorted, and/or selected using one or more supervised and/or unsupervised machine-learning processes and/or models as described in further detail below; such models may include without limitation a training data classifier 716. Training data classifier 716 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 700 may generate a classifier using a classification algorithm, defined as a processes whereby a computing device and/or any module and/or component operating thereon derives a classifier from training data 704. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 716 may classify elements of training data to subject demographic categories.

Still referring to FIG. 7, Computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A)$ $P(A)=P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device may then calculate a likelihood table by calculating probabilities of different data entries and classification labels. Computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 7, Computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 7, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 7, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 7, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 7, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 7, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 7, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 7, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 7, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 7, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $X_{max}$:

$$X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation $\sigma$ of a set or subset of values:

$$X_{new} = \frac{X - X_{mean}}{\sigma}.$$

Scaling may be performed using a median value of a a set or subset $X_{median}$ and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 7, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 7, machine-learning module 700 may be configured to perform a lazy-learning process 720 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 704. Heuristic may include selecting some number of highest-ranking associations and/or training data 704 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 7, machine-learning processes as described in this disclosure may be used to generate machine-learning models 724. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 724 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 724 may be generated by creating an artificial neural network, such as a convolutional neural network comprising an input layer of nodes, one or more intermediate layers, and an output layer of nodes. Connections between nodes may be created via the process of "training" the network, in which elements from a training data 704 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 7, machine-learning algorithms may include at least a supervised machine-learning process 728. At least a supervised machine-learning process 728, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include ultrasonic images as described above as inputs, 3D models, such as those generated based on historical CT scan data as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 704. Persons skilled in the art, upon reviewing the entirety of this disclosure, will be aware of various possible variations of at least a supervised machine-learning process 728 that may be used to determine relation between inputs and outputs. Supervised machine-learning processes may include classification algorithms as defined above.

With further reference to FIG. 7, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 7, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 7, machine learning processes may include at least an unsupervised machine-learning processes 732. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 732 may not require a response variable; unsupervised processes 732 may be used to find interesting patterns and/or inferences between variables, to determine a degree of correlation between two or more variables, or the like.

Still referring to FIG. 7, machine-learning module 700 may be designed and configured to create a machine-learning model 724 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 7, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 7, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0"

voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 7, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 7, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 7, one or more processes or algorithms described above may be performed by at least a dedicated hardware unit 736. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 736 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 736 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 736 to perform one or more operations described herein, such as evaluation of model and/or algorithm outputs, one-time or iterative updates to parameters, coefficients, weights, and/or biases, and/or any other operations such as vector and/or matrix operations as described in this disclosure.

With continued reference to FIG. 7, apparatus 100 may use user feedback to train the machine-learning models and/or classifiers described above. For example, classifier may be trained using past inputs and outputs of classifier. In some embodiments, if user feedback indicates that an output of classifier was "bad," then that output and the corresponding input may be removed from training data used to train classifier, and/or may be replaced with a value entered by, e.g., another user that represents an ideal output given the input the classifier originally received, permitting use in retraining, and adding to training data; in either case, classifier may be retrained with modified training data as described in further detail below. In some embodiments, training data of classifier may include user feedback.

With continued reference to FIG. 7, in some embodiments, an accuracy score may be calculated for classifier using user feedback. For the purposes of this disclosure, "accuracy score," is a numerical value concerning the accuracy of a machine-learning model. For example, a plurality of user feedback scores may be averaged to determine an accuracy score. In some embodiments, a cohort accuracy score may be determined for particular cohorts of persons. For example, user feedback for users belonging to a particular cohort of persons may be averaged together to determine the cohort accuracy score for that particular cohort of persons and used as described above. Accuracy score or another score as described above may indicate a degree of retraining needed for a machine-learning model such as a classifier; apparatus 100 may perform a larger number of retraining cycles for a higher number (or lower number, depending on a numerical interpretation used), and/or may collect more training data for such retraining, perform more training cycles, apply a more stringent convergence test such as a test requiring a lower mean squared error, and/or indicate to a user and/or operator that additional training data is needed.

Referring now to FIG. 8, an exemplary embodiment of neural network 800 is illustrated. A neural network 800 also known as an artificial neural network, is a network of "nodes," or data structures having one or more inputs, one or more outputs, and a function determining outputs based on inputs. Such nodes may be organized in a network, such as without limitation a convolutional neural network (CNN), including an input layer of nodes 804, one or more intermediate layers 808, and an output layer of nodes 812. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes.

Figure 9:
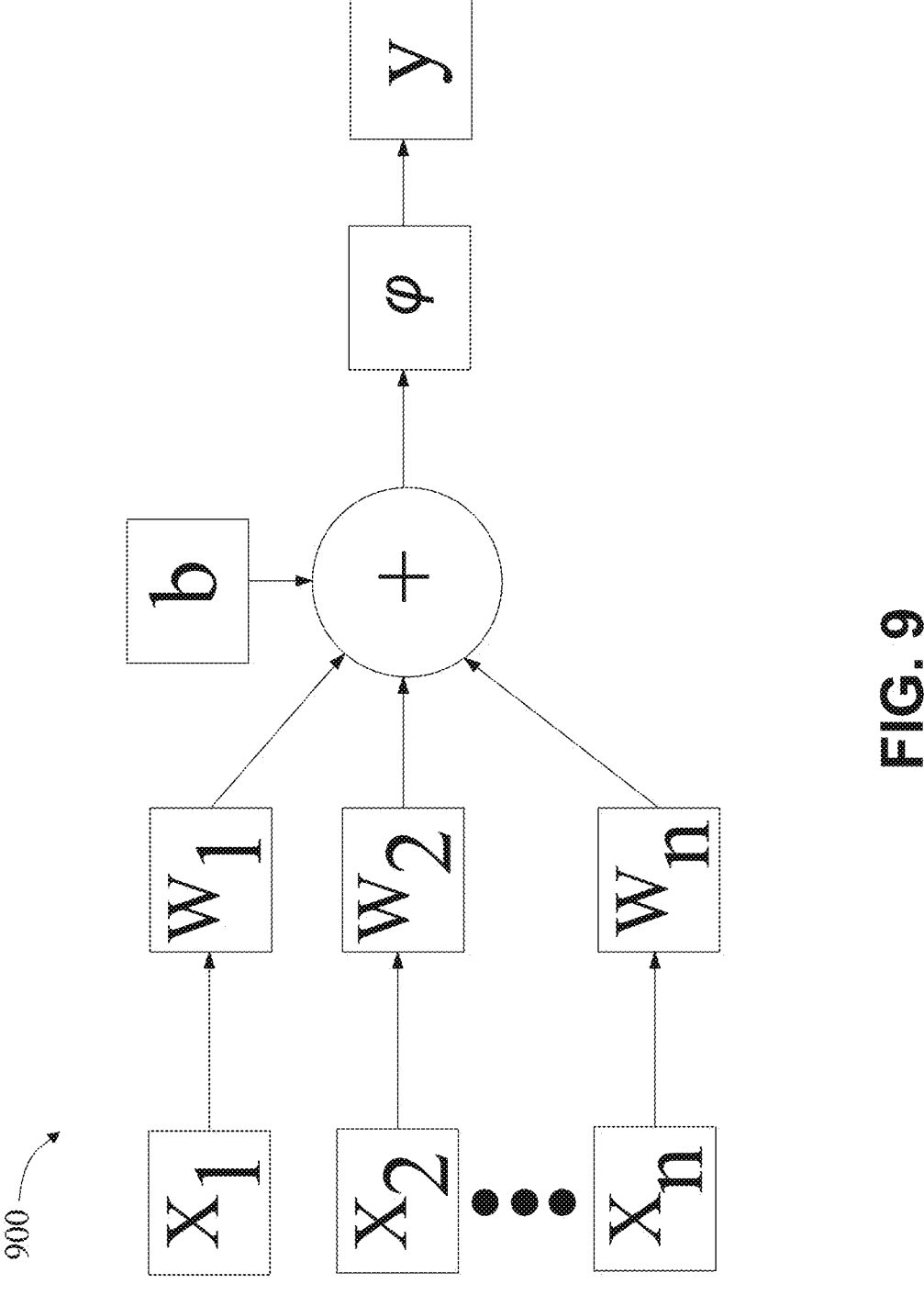
FIG. 9 is a schematic diagram of an exemplary embodiment of a neural network node.

Referring now to FIG. 9, an exemplary embodiment of a node 900 of a neural network is illustrated. A node may include, without limitation a plurality of inputs x; that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(ax, x)$ for some a, an exponential linear units function such as $$f(x) = \begin{cases} x \text{ for } x \geq 0 \\ \alpha(e^x - 1) \text{ for } x < 0 \end{cases}$$

for some value of $\alpha$ (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x)=x*\text{sigmoid}(x)$, a Gaussian error linear unit function such as $f(x)=a(1+\tanh(\sqrt{2/\pi}(x+bx^r)))$ for some values of a, b, and r, and/or a scaled exponential linear unit function such as $$f(x) = \lambda \begin{cases} \alpha(e^x - 1) \text{ for } x < 0 \\ x \text{ for } x \geq 0 \end{cases}.$$

Fundamentally, there is no limit to the nature of functions of inputs x; that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function $\varphi$, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Still referring to FIG. 9, a "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like. CNN may include, without limitation, a deep neural network (DNN) extension, where a DNN is defined as a neural network with two or more hidden layers.

Still referring to FIG. 9, in some embodiments, a convolutional neural network may learn from images. In non-limiting examples, a convolutional neural network may perform tasks such as classifying images, detecting objects depicted in an image, segmenting an image, and/or processing an image. In some embodiments, a convolutional neural network may operate such that each node in an input layer is only connected to a region of nodes in a hidden layer. In some embodiments, the regions in aggregate may create a feature map from an input layer to the hidden layer. In some embodiments, a convolutional neural network may include a layer in which the weights and biases for all nodes are the same. In some embodiments, this may allow a convolutional neural network to detect a feature, such as an edge, across different locations in an image.

Still referring to FIG. 9, 3D Cardiac Model Generation Machine Learning Model may include a CNN, such as a 3D CNN. In some embodiments, 3D CNN, unlike a standard 2D CNN, may include utilization of one or more 3D convolutions which allow them to directly process 3D data, thereby enabling processor to generate 3D structures such as 3D data structure a heart using the 3D CNN. In a non-limiting example, 3D CNN may include one or more 3D filters (i.e., kernels) that move through ultrasonic images in three dimensions and capturing spatial relationships in x, y, and z axis. Similar to 3D convolutions, 3D CNN may further include one or more 3D pooling layers that may be used to reduce the dimensionality of ultrasonic images while preserving spatial features as described above. Additionally, or alternatively, an encoder-decoder structure may be implemented (extended to 3D) in 3D CNN, wherein the encoder-decoder structure includes an encoding path that captures the context and a decoding path that enables precise localization in a same manner as U-net as described above. Such encoder-decoder structures may also include a plurality of skip connections, allowing 3D CNN to use information from multiple resolutions to improve the process of generating 3D data structure of a heart.

With continued reference to FIG. 9, in an embodiment, training a 3D cardiac model generation machine learning model may include selecting a suitable loss function to guide the training process. In a non-limiting example, a loss function that measures the difference between the predicted 3D VORs and the ground truth 3D structure e.g., CT-based 3D models may be used, such as, without limitation, mean squared error (MSE) or a custom loss function may be designed for one or more embodiments described herein. Additionally, or alternatively, optimization algorithms, such as stochastic gradient descent (SGD), may then be used to adjust the model's parameters to minimize such loss. In a further non-limiting embodiment, instead of directly predicting 3D data structure, 3D cardiac model generation machine learning model may be trained as a regression model to predict presence indicators and/or other embedded values described herein for each voxel of plurality of voxels within a 3D grid. Additionally, CNN may be extended with additional deep learning techniques, such as recurrent neural networks (RNNs) or attention mechanism, to capture additional features and/or data relationships within input data.

These extensions may further enhance the accuracy and robustness of the 3D modeling.

Referring now to FIG. 10, an exemplary embodiment of a method 1000 of determining a cardiac implant size is illustrated. One or more steps if method 1000 may be implemented, without limitation, as described with reference to other figures. One or more steps of method 1000 may be implemented, without limitation, using at least a processor.

Still referring to FIG. 10, in some embodiments, method 1000 may include a step 1005 of collecting a plurality of ultrasonic images. In some embodiments, step 1005 may be performed through use of an ultrasonic imaging device. In some embodiments, a plurality of ultrasonic images includes transesophageal echocardiogram (TEE) images. In some embodiments, a plurality of ultrasonic images includes intracardiac echo (ICE) images. In some embodiments, the plurality of ultrasonic images comprises ultrasonic images captured at the same position and different orientations with respect to a subject's heart. In some embodiments, the plurality of ultrasonic images comprises a view of a subject's heart at 0°, 45°, 90°, and 135° on a mid-esophageal view.

Still referring to FIG. 10, in some embodiments, method 1000 may include a step 1010 of, using a 3D cardiac model generation machine learning model trained on a training dataset comprising example ultrasonic images correlated with example 3D cardiac models, generating a 3D cardiac model based on the plurality of ultrasonic images. In some embodiments, the example 3D cardiac models include computed tomography (CT) scan data. In some embodiments, generating a 3D cardiac model based on the plurality of ultrasonic images includes generating a set of shape parameters representing a cardiac shape as a function of the plurality of ultrasonic images and a shape identification model trained on the training dataset; and the set of shape parameters comprises a plurality of numerical descriptors representing at least a geometric characteristic of a subject's heart and a plurality of associated parameter ranges. In some embodiments of method 10000, step 1010 may include generating a 3D voxel occupancy representation (VOR) representing a cardiac shape as a function of plurality of ultrasonic images and 3D cardiac model generation machine learning model trained on the training dataset, generating a mesh representing the cardiac shape as a function of the 3D voxel occupancy representation, and displaying, using display, the mesh to a user.

Still referring to FIG. 10, in some embodiments, method 1000 may include a step 1015 of generating at least a cardiac measurement based on the 3D cardiac model. In some embodiments, the cardiac measurement comprises an ostial diameter of a left atrial appendage (LAA).

Still referring to FIG. 10, in some embodiments, method 1000 may include a step 1020 of determining a cardiac implant size based on the at least a cardiac measurement.

Still referring to FIG. 10, in some embodiments, method 1000 may include a step 1025 of displaying to a user the cardiac implant size. In some embodiments, a cardiac implant size comprises a left atrial appendage occlusion device size.

Still referring to FIG. 10, in some embodiments, method 1000 may further include determining a cardiac implant placement as a function of the 3D cardiac model. In some embodiments, method 1000 may further include determining a cardiac implant candidate quality as a function of the 3D cardiac model. In some embodiments, method 1000 may further include generating an example ultrasonic image of the training dataset as a function of historical computed tomography (CT) scan data.

Still referring to FIG. 10, in some embodiments, method 1000 may include receiving at least an ultrasound localization datum representing one or both of position and angle of ultrasonic imaging device, and generating, using 3D cardiac model generation machine learning model, 3D cardiac model as a function of the at least an ultrasound localization datum.

Still referring to FIG. 10, in some embodiments, method 1000 may include calculating a level of uncertainty at a plurality of locations on 3D cardiac model, where the plurality of locations comprises a high uncertainty region, receiving a subsequent plurality of ultrasonic images of cardiac anatomy corresponding to the high uncertainty region of the 3D cardiac model, where the subsequent plurality of ultrasonic images is captured using ultrasonic imaging device as a function of the high uncertainty region, and generating a subsequent 3D cardiac model as a function of the subsequent plurality of ultrasonic images.

Still referring to FIG. 10, in some embodiments, method 1000 may include receiving a 3D cardiac implant model representing a cardiac implant and displaying, using a display, the 3D cardiac implant model positioned within 3D cardiac model.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 11:
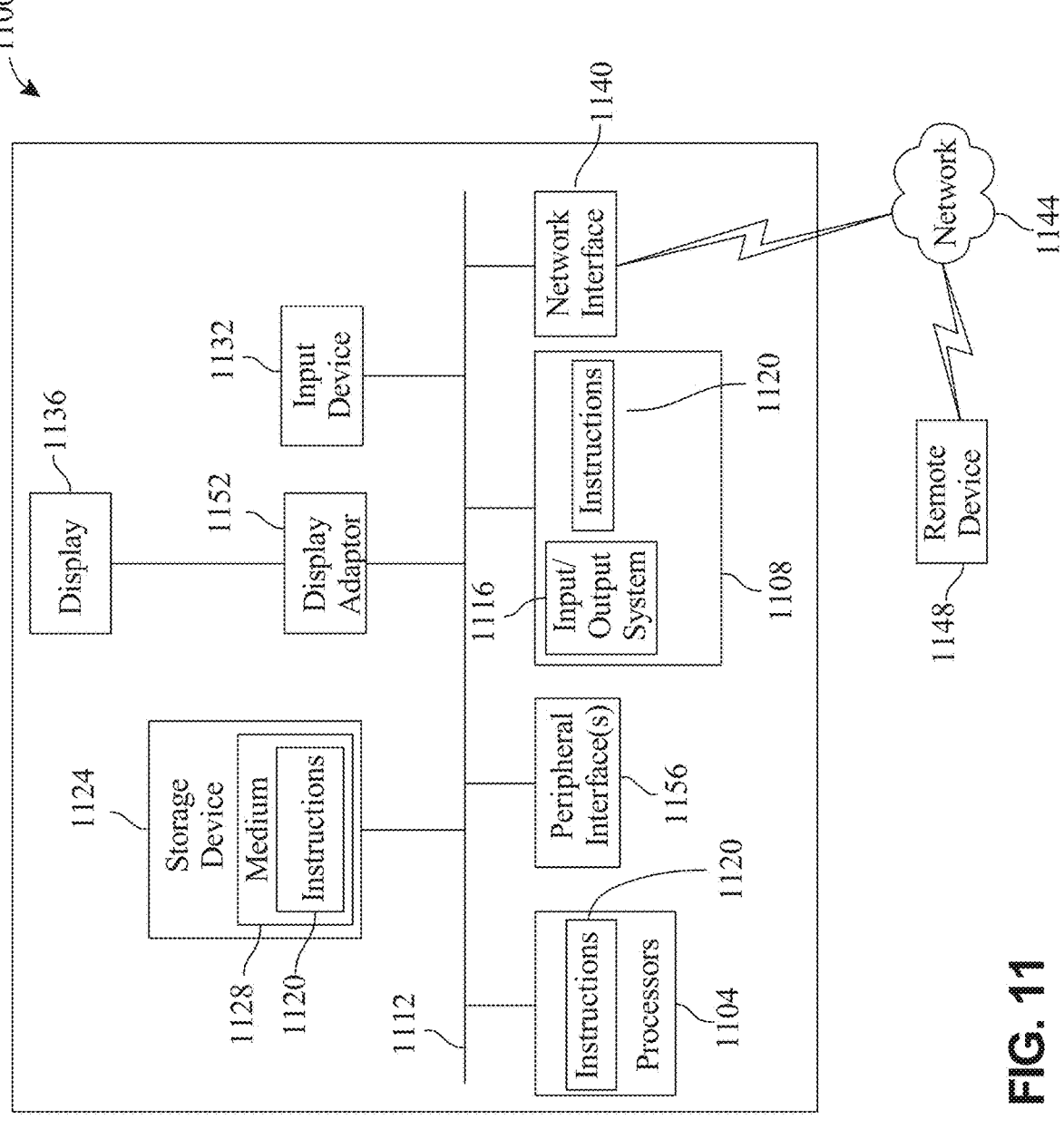
FIG. 11 is a block diagram of a computing system that can be used to implement any one or more of the methodologies disclosed herein and any one or more portions thereof.

FIG. 11 shows a diagrammatic representation of one embodiment of a computing device in the exemplary form of a computer system 1100 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1100 includes a processor 1104 and a memory 1108 that communicate with each other, and with other components, via a bus 1112. Bus 1112 may include any of several types of bus structures including, but not limited to, a memory bus, a memory controller, a peripheral bus, a local bus, and any combinations thereof, using any of a variety of bus architectures.

Processor 1104 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1104 may be organized according to Von Neumann and/or Harvard architecture as a non-limiting example. Processor 1104 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 1108 may include various components (e.g., machine-readable media) including, but not limited to, a random-access memory component, a read only component, and any combinations thereof. In one example, a basic input/output system 1116 (BIOS), including basic routines that help to transfer information between elements within computer system 1100, such as during start-up, may be stored in memory 1108. Memory 1108 may also include (e.g., stored on one or more machine-readable media) instructions (e.g., software) 1120 embodying any one or more of the aspects and/or methodologies of the present disclosure. In another example, memory 1108 may further include any number of program modules including, but not limited to, an operating system, one or more application programs, other program modules, program data, and any combinations thereof.

Computer system 1100 may also include a storage device 1124. Examples of a storage device (e.g., storage device 1124) include, but are not limited to, a hard disk drive, a magnetic disk drive, an optical disc drive in combination with an optical medium, a solid-state memory device, and any combinations thereof. Storage device 1124 may be connected to bus 1112 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1124 (or one or more components thereof) may be removably interfaced with computer system 1100 (e.g., via an external port connector (not shown)). Particularly, storage device 1124 and an associated machine-readable medium 1128 may provide nonvolatile and/or volatile storage of machine-readable instructions, data structures, program modules, and/or other data for computer system 1100. In one example, software 1120 may reside, completely or partially, within machine-readable medium 1128. In another example, software 1120 may reside, completely or partially, within processor 1104.

Computer system 1100 may also include an input device 1132. In one example, a user of computer system 1100 may enter commands and/or other information into computer system 1100 via input device 1132. Examples of an input device 1132 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1132 may be interfaced to bus 1112 via any of a variety of interfaces (not shown) including, but not limited to, a serial interface, a parallel interface, a game port, a USB interface, a FIRE-WIRE interface, a direct interface to bus 1112, and any combinations thereof. Input device 1132 may include a touch screen interface that may be a part of or separate from display device 1136, discussed further below. Input device 1132 may be utilized as a user selection device for selecting one or more graphical representations in a graphical interface as described above.

A user may also input commands and/or other information to computer system 1100 via storage device 1124 (e.g., a removable disk drive, a flash drive, etc.) and/or network interface device 1140. A network interface device, such as network interface device 1140, may be utilized for connecting computer system 1100 to one or more of a variety of networks, such as network 1144, and one or more remote devices 1148 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1144, may employ a wired and/or a wireless mode of communication. In general, any network topology may be used. Information (e.g., data, software 1120, etc.) may be communicated to and/or from computer system 1100 via network interface device 1140.

Computer system 1100 may further include a video display adapter 1152 for communicating a displayable image to a display device, such as display device 1136. Examples of a display device include, but are not limited to, a liquid crystal display (LCD), a cathode ray tube (CRT), a plasma display, a light emitting diode (LED) display, and any combinations thereof. Display adapter 1152 and display device 1136 may be utilized in combination with processor 1104 to provide graphical representations of aspects of the present disclosure. In addition to a display device, computer system 1100 may include one or more other peripheral output devices including, but not limited to, an audio speaker, a printer, and any combinations thereof. Such peripheral output devices may be connected to bus 1112 via a peripheral interface 1156. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for determining a cardiac implant size, the apparatus comprising:

an ultrasonic imaging device;

at least a processor; and a memory communicatively connected to the at least a processor, wherein the memory contains instructions configuring the at least a processor to:

using the ultrasonic imaging device, collect a plurality of ultrasonic images;

using a 3D cardiac model generation machine learning model trained on a training dataset comprising example ultrasonic images correlated with example 3D cardiac models, generate a 3D cardiac model based on the plurality of ultrasonic images;

generate at least a cardiac measurement and a cardiac implant placement comprising at least a location of a cardiac implant and a location of a component of the cardiac implant based on the 3D cardiac model;

determine the cardiac implant size and a cardiac implant candidate quality based on the at least a cardiac measurement;

determine a thrombus status using a thrombus machine learning model based on the plurality of plurality of ultrasonic images; and using a display, display to a user the cardiac implant size, the cardiac implant candidate quality, the cardiac implant placement and the thrombus status.

2. The apparatus of claim 1, wherein the cardiac implant size comprises a left atrial appendage occlusion device size.

3. The apparatus of claim 1, wherein the memory contains instructions further configuring the processor to determine one or both of a cardiac implant placement and a cardiac implant candidate as a function of the 3D cardiac model.

4. The apparatus of claim 1, wherein the memory contains instructions further configuring the processor to:

receive at least an ultrasound localization datum representing one or both of position and angle of the ultrasonic imaging device; and generate, using the 3D cardiac model generation machine learning model, the 3D cardiac model as a function of the at least an ultrasound localization datum.

5. The apparatus of claim 1, wherein the plurality of ultrasonic images comprises one or more of transthoracic echocardiogram (TTE) images and point of care ultrasound (POCUS) images.

6. The apparatus of claim 1, wherein the memory contains instructions further configuring the processor to:

calculate a level of uncertainty at a plurality of locations on the 3D cardiac model, wherein the plurality of locations comprises a high uncertainty region and the level of uncertainty comprises one or more of epistemic uncertainty, aleatoric uncertainty, model parameter uncertainty, boundary uncertainty, uncertainty in time series data, predictive uncertainty, systematic uncertainty, model output uncertainty;

receive a subsequent plurality of ultrasonic images of cardiac anatomy corresponding to a high uncertainty region of the 3D cardiac model, wherein the subsequent plurality of ultrasonic images is captured using the ultrasonic imaging device, as a function of the high uncertainty region; and generate a subsequent 3D cardiac model as a function of the subsequent plurality of ultrasonic images.

7. The apparatus of claim 1, wherein generating the 3D cardiac model based on the plurality of ultrasonic images comprises:

generating a set of shape parameters representing a cardiac shape as a function of the plurality of ultrasonic images and a shape identification model trained on the training dataset;

wherein the set of shape parameters comprises a plurality of numerical descriptors representing at least a geometric characteristic of a subject's heart and a plurality of associated parameter ranges, wherein at least a parameter range of the plurality of associated parameter ranges is based on a subset of possible values of a parameter that historical healthy structures commonly fall into, as determined from a dataset.

8. The apparatus of claim 1, wherein the memory contains instructions further configuring the processor to:

receive a 3D cardiac implant model representing a cardiac implant; and display, using the display, the 3D cardiac implant model positioned within the 3D cardiac model.

9. The apparatus of claim 1, wherein the cardiac measurement comprises an ostial diameter of a left atrial appendage (LAA).

10. The apparatus of claim 1, wherein generating the 3D cardiac model based on the plurality of ultrasonic images comprises:

generating a 3D voxel occupancy representation (VOR) representing a cardiac shape as a function of the plurality of ultrasonic images and the 3D cardiac model generation machine learning model trained on the training dataset;

generating a mesh representing the cardiac shape as a function of the 3d voxel occupancy representation; and displaying, using the display, the mesh to the user.

11. A method of determining a cardiac implant size, the method comprising:

using at least a processor and an ultrasonic imaging device, collecting a plurality of ultrasonic images;

using the at least a processor and a 3D cardiac model generation machine learning model trained on a training dataset comprising example ultrasonic images correlated with example 3D cardiac models, generating a 3D cardiac model based on the plurality of ultrasonic images;

using the at least a processor, generating at least a cardiac measurement based on the 3D cardiac model and a cardiac implant placement comprising at least a location of a cardiac implant and a location of a component of the cardiac implant;

using the at least a processor, determining the cardiac implant size and a cardiac implant candidate quality based on the at least a cardiac measurement;

using the at least a processor, determining a thrombus status using a thrombus machine learning model based on the plurality of plurality of ultrasonic images; and using the at least a processor and a display, displaying to a user the cardiac implant, the cardiac implant candidate quality, the cardiac implant placement and the thrombus status.

12. The method of claim 11, wherein the cardiac implant size comprises a left atrial appendage occlusion device size.

13. The method of claim 11, wherein the method further comprises determining one or both of a cardiac implant placement and a cardiac implant candidate quality as a function of the 3D cardiac model.

14. The method of claim 11, wherein the method further comprises:

receiving, using the at least a processor, at least an ultrasound localization datum representing one or both of position and angle of the ultrasonic imaging device; and generating, using the at least a processor and the 3D cardiac model generation machine learning model, the 3D cardiac model as a function of the at least an ultrasound localization datum.

15. The method of claim 11, wherein the plurality of ultrasonic images comprises one or more of transthoracic echocardiogram (TTE) images, and point of care ultrasound (POCUS) images.

16. The method of claim 11, wherein the method further comprises:

calculating, using the at least a processor, a level of uncertainty at a plurality of locations on the 3D cardiac model, wherein the plurality of locations comprises a high uncertainty region, and the level of uncertainty comprises one or more of epistemic uncertainty, aleatoric uncertainty, model parameter uncertainty, boundary uncertainty, uncertainty in time series data, predictive uncertainty, systematic uncertainty, model output uncertainty;

receiving, using the at least a processor, a subsequent plurality of ultrasonic images of cardiac anatomy corresponding to a high uncertainty region of the 3D cardiac model, wherein the subsequent plurality of ultrasonic images is captured using the ultrasonic imaging device, as a function of the high uncertainty region; and generating, using the at least a processor, a subsequent 3D cardiac model as a function of the subsequent plurality of ultrasonic images.

17. The method of claim 11, wherein generating the 3D cardiac model based on the plurality of ultrasonic images comprises:

generating a set of shape parameters representing a cardiac shape as a function of the plurality of ultrasonic images and a shape identification model trained on the training dataset;

wherein the set of shape parameters comprises a plurality of numerical descriptors representing at least a geometric characteristic of a subject's heart and a plurality of associated parameter ranges, wherein at least a parameter range of the plurality of associated parameter ranges is based on a subset of possible values of a parameter that historical healthy structures commonly fall into, as determined from a dataset.

18. The method of claim 11, wherein the method further comprises:

receiving, using the at least a processor, a 3D cardiac implant model representing a cardiac implant; and displaying, using the at least a processor and the display, the 3D cardiac implant model positioned within the 3D cardiac model.

19. The method of claim 11, wherein the cardiac measurement comprises an ostial diameter of a left atrial appendage (LAA).

20. The method of claim 11, wherein the generating the 3D cardiac model based on the plurality of ultrasonic images comprises:

generating, using the at least a processor, a 3D voxel occupancy representation (VOR) representing a cardiac shape as a function of the plurality of ultrasonic images and the 3D cardiac model generation machine learning model trained on the training dataset;

generating, using the at least a processor, a mesh representing the cardiac shape as a function of the 3D voxel occupancy representation; and displaying, using the at least a processor and the display, the mesh to the user.

* * * * *